(12) United States Patent
Seela et al.

(10) Patent No.: US 7,612,187 B2
(45) Date of Patent: Nov. 3, 2009

(54) 2-AZAPURINE COMPOUNDS AND THEIR USES

(75) Inventors: Frank Seela, Osnabrueck (DE); Helmut Rosemeyer, Osnabrueck (DE); Enno Schweinberger, Oberweser (DE); Dieter Heindl, Tutzing (DE); Frank Bergmann, Iffeldorf (DE)

(73) Assignee: Roche Diagnostics, GmbH, Mannheim (DE)

( * ) Notice: Subject to any disclaimer, the term of this patent is extended or adjusted under 35 U.S.C. 154(b) by 238 days.

(21) Appl. No.: 11/441,755

(22) Filed: May 25, 2006

(65) Prior Publication Data

US 2007/0015725 A1 Jan. 18, 2007

Related U.S. Application Data

(63) Continuation of application No. 10/070,340, filed as application No. PCT/EP00/08371 on Aug. 28, 2000, now Pat. No. 7,169,553.

(30) Foreign Application Priority Data

Aug. 30, 1999 (EP) .................... 99116767

(51) Int. Cl.
*C07H 21/02* (2006.01)
*C07H 21/04* (2006.01)
*C07H 21/00* (2006.01)
*C12Q 1/68* (2006.01)
*C12P 19/34* (2006.01)

(52) U.S. Cl. ............... 536/23.1; 536/24.3; 536/24.33; 536/25.3; 435/6; 435/91.2

(58) Field of Classification Search .............. 435/6, 435/91.1, 91.2; 536/23.1, 24.3, 24.33, 25.3
See application file for complete search history.

(56) References Cited

U.S. PATENT DOCUMENTS 4,458,066 A 7/1984 Caruthers et al.
4,683,202 A 7/1987 Mullis

FOREIGN PATENT DOCUMENTS

DE 3943522 A1 7/1991
EP 0 286 028 B1 3/1988
EP 0 324 474 B1 12/1989

(Continued)

OTHER PUBLICATIONS

Acedo et al. (1995) "Synthesis and Biophysical Properties of Ologonucleotides Containing 2-Aza-2'-Deoxyinosine." *Journal of Organic Chemistry*, 60: 6262-6269.

(Continued)

*Primary Examiner*—Jezia Riley
(74) *Attorney, Agent, or Firm*—Olga Kay; Charles M. Doyle

(57) ABSTRACT

Within oligonucleotides 2-azapurine and especially 2-azaadenine bases form specifically base pairs with guanine. This base pair is of analogous stability as an adenine-thymine but less stable than a guanine-cytosine base pair. Therefore, the incorporation of 2-azaadenine residues into oligonucleotides instead of cytosine leads specifically to hybridization complexes with nucleic acids with homogenous stability. This is useful for the adaptation of the stabilities of different oligonucleotide sequences in all kinds of hybridization techniques, for example in oligomer chip technology.

13 Claims, 6 Drawing Sheets

FOREIGN PATENT DOCUMENTS

| EP | 0 476 014 B1 | 7/1990 |
|---|---|---|
| EP | 0 624 161 B1 | 9/1992 |
| EP | 0 680 969 A2 | 4/1995 |
| WO | WO 92/02638 A1 | 8/1990 |
| WO | WO 92/20702 A1 | 5/1992 |

OTHER PUBLICATIONS

Beaucage et al. (1981) "Deoxynucleoside Phoshoramidites—A New Class of Key Intermediates for Deoxypolynucleotide Synthesis." *Tetrahedron Letters*, 22(20): 1859-1862.

Bennett et al. (1976) "Nucleosides of 2-Aza-Purines—Cytotoxicities and Activities as Substrates for Enzymes Metabolizing Purine Nucleosides." *Biochemical Pharmacology*, 25(5): 517-521.

Brown et al. (1979) "Chemical Synthesis and Cloning of a Tyrosine tRNA Gene." *Methods In Enzymology*, 68: 109-151.

Bussolari et al. (1996) "The Synthesis and Biological Evaluation of 4-*p*-Nitrobenzylthio-v-triazolo(4,5-d) pyrodazine and Imidazo(4,5-d) pyridazine Ribosides as Potential Nucleoside Transport Inhibitors." *Bioorganic & Medicinal Chemistry*, 4(1): 1725-1731.

Carbon (1960) "Synthesis of Some Imidazo(4, 5-d) Pyridazines and Imidazo (4,5-d) trazolo (4,3-b) pyridazines." *Journals of Organic Chemistry*, 25(4): 579-582.

Chollet et al. (1998) "DNA containing the base analogue 2-aminoadenine: preparation, use as hybridization probes and cleavage by restriction endonucleases." *Nucleic Acids Research*, 16(1): 305-317.

Eritja et al. (1995) "Preparation of Oligonucleotides Containing Non-Natural Base Analogues." *Nucleosides and Nucleotides*, 14(3-5): 821-824.

Feranadez-Forner et al. (1991) "Preparation of Oligonucleotides Containing dAICA Using an Unexpected Side-Reaction Observed on a Projected Derivative of 2-Aza-2'Deoxyinosine." *Tetrahedron*, 47(42): 8917-8930.

Fukui et al. (1978) "XLIV Synthesis and Properties of Poly(2-Azaadentlic Acid) and Poly(2-Azainosinic Acid)." *Biochimica et Biophysica Acta*, 520: 441-451.

Hoheisel (1996) "Sequence-Independence and Linear Variation of Oligonucleotide DNA Binding Stabilities." *Nucleic Acids Research*, 24(3): 430-432.

Hoheisel (1997) "Oligomer-Chip Technology." *Tibtech*, 15: 465-469.

Kazimierczuk et al. (1990) "Steroselective Synthesis of 2-Azapurine 2'Deoxy-β-D-Ribonucleosides by Nucleobase-Anion Glycosylation." *Liebigs Ann. Chem*, 647-651.

Lin et al. (1999) "Synthesis and Properties of a Novel Phosphodiester Analogue, Nucleoside Boranophosphorothioate." *Chemical Communicaitons*, 1517-1518.

Montgomery et al. (1975) "Nucleosides of 2-Azapurines. 7H-Imidazo4,5-D-1,2,3-Triaznes." *Journal of Medicinal Chemistry, American Chemical Society* 18(6): 564-567.

Narang et al. (1979) "Improved Phosphotriester Method for the Synthesis of Gene Fragements." *Methods in Enzymology*, 68:90-98.

Saunders et al. (1986) "Mechanisms of 5-(3,3,-Dimethyl-1-trazeno) imidazole-4-car boxamide (Dicarbazine) Cytotoxicity Toward Chinese Hamster Ovary Cells in Vitro are Dictates by Incubation Conditions." *Chemico-Biological Interactions*, 58(3): 319-331.

Seela et al. (1999) "Synthesis, Base Pairing and Stacking Properties of Oligonucleotides Containing 2-Aza-2'-deoxyadenosin." *Collection Symposium Series*, 2: 124-128.

Seela et al. (2000) "Synthesis, Base-Pairing and Stacking Properties of Oligonucleotides Containing 2-Aza-2'-deoxyadenosine." *Chemical Abstracts*, 133: Abstract No. 89731z.

Sugiyama et al. (2000) "2-Aza-2'-Deoxyadenosine: Synthesis, Base-Pairing Selectivity, and Stacking Properties of Oligonucleotides." *Chemistry A European Journal*, 6(2): 369-378.

Yamaji et al. (1975) "The Synthesis of 2-Aza-Adenosine-3', 5'-Cyclic Phosphate via 1, $N^6$—Etheno-Adenosine-3', 5'-Cylic Phosphate." *Chemistry Letters*, 311-314.

1  2  3  4 purine numbering   systematic numbering

NBS: N-bromosuccinimide dG   z²A_d
Watson-Crick mode
motif I, antiparallel stranded dG   isoG_d
Watson-Crick mode
motif II, antiparallel stranded

SEQUENCE LISTING

<160> NUMBER OF SEQ ID NOS: 10

<210> SEQ ID NO 1
<211> LENGTH: 12
<212> TYPE: DNA
<213> ORGANISM: Artificial Sequence
<220> FEATURE:
<223> OTHER INFORMATION: Description of artificial sequence:
      Synthetic oligonucleotide used
      in establishing thermodynamic properties of duplexes.

<400> SEQUENCE: 1
taggtcaata ct                                                          12

<210> SEQ ID NO 2
<211> LENGTH: 12
<212> TYPE: DNA
<213> ORGANISM: Artificial Sequence
<220> FEATURE:
<223> OTHER INFORMATION: Description of artificial sequence:
      Synthetic oligonucleotide used
      in establishing thermodynamic properties of duplexes.

<400> SEQUENCE: 2
atccagttat ga                                                          12

<210> SEQ ID NO 3
<211> LENGTH: 12
<212> TYPE: DNA
<213> ORGANISM: Artificial Sequence
<220> FEATURE:
<223> OTHER INFORMATION: Description of artificial sequence:
      Synthetic oligonucleotide used
      in establishing thermodynamic properties of duplexes.
<220> FEATURE:
<221> NAME/KEY: modified_base
<222> LOCATION: (7)..(7)
<223> OTHER INFORMATION: n = 2-Aza 2'-deoxyadenosine

<400> SEQUENCE: 3
taggtcnata ct                                                          12

<210> SEQ ID NO 4
<211> LENGTH: 12
<212> TYPE: DNA
<213> ORGANISM: Artificial Sequence
<220> FEATURE:
<223> OTHER INFORMATION: Description of artificial sequence:
      Synthetic oligonucleotide used
      in establishing thermodynamic properties of duplexes.

<400> SEQUENCE: 4
atccaggtat ga                                                          12

<210> SEQ ID NO 5
<211> LENGTH: 12
<212> TYPE: DNA
<213> ORGANISM: Artificial Sequence
<220> FEATURE:
<223> OTHER INFORMATION: Description of artificial sequence:
      Synthetic oligonucleotide used
      in establishing thermodynamic properties of duplexes.
<220> FEATURE:
<221> NAME/KEY: modified_base
<222> LOCATION: (7)..(8)
<223> OTHER INFORMATION: n = 2-Aza 2'-deoxyadenosine

<400> SEQUENCE: 5

```
taggtcnnta ct                                                         12

<210> SEQ ID NO 6
<211> LENGTH: 12
<212> TYPE: DNA
<213> ORGANISM: Artificial Sequence
<220> FEATURE:
<223> OTHER INFORMATION: Description of artificial sequence:
      Synthetic oligonucleotide used
      in establishing thermodynamic properties of duplexes.

<400> SEQUENCE: 6
atccagaaat ga                                                         12

<210> SEQ ID NO 7
<211> LENGTH: 12
<212> TYPE: DNA
<213> ORGANISM: Artificial Sequence
<220> FEATURE:
<223> OTHER INFORMATION: Description of artificial sequence:
      Synthetic oligonucleotide used
      in establishing thermodynamic properties of duplexes.

<400> SEQUENCE: 7
atccagccat ga                                                         12

<210> SEQ ID NO 8
<211> LENGTH: 12
<212> TYPE: DNA
<213> ORGANISM: Artificial Sequence
<220> FEATURE:
<223> OTHER INFORMATION: Description of artificial sequence:
      Synthetic oligonucleotide used
      in establishing thermodynamic properties of duplexes.

<400> SEQUENCE: 8
atccagggat ga                                                         12

<210> SEQ ID NO 9
<211> LENGTH: 12
<212> TYPE: DNA
<213> ORGANISM: Artificial Sequence
<220> FEATURE:
<223> OTHER INFORMATION: Description of artificial sequence:
      Synthetic oligonucleotide used
      in establishing thermodynamic properties of duplexes.

<400> SEQUENCE: 9
taggtcggta ct                                                         12

<210> SEQ ID NO 10
<211> LENGTH: 12
<212> TYPE: DNA
<213> ORGANISM: Artificial Sequence
<220> FEATURE:
<223> OTHER INFORMATION: Description of artificial sequence:
      Synthetic oligonucleotide used
      to construct a hybrid with SEQ ID NO: 1

<400> SEQUENCE: 10
agtattgacc ta                                                         12
```

2-AZAPURINE COMPOUNDS AND THEIR USES

CROSS-REFERENCE TO RELATED APPLICATIONS

This application is a Continuation Application of, and claims benefit and priority from, U.S. Utility Application 10/070,340, "2-Azapurine Compounds and Their Use", to Frank Seela, et al., filed Jun. 4, 2002; which is a national stage application filed under 35 USC § 371 of PCT/EP00/08371, filed Aug. 28, 2000; which claims benefit and priority of European Patent Office application number 99116767.7, filed Aug. 30, 1999. The full disclosure of the prior applications are incorporated herein by reference.

The present invention is directed to a nucleic acid binding compound comprising 2-azapurines, a compound useful for the preparation of such compound, a binding product of this nucleic acid binding compound with a nucleic acid, a method for the determination of a nucleic acid using said compound, and several uses of 2-azapurine compounds.

Some 2-azapurine compounds are known in the art. In Chemistry of Nucleosides and Nucleotides (Vol. 2, p. 288-297, and p. 319) there are shown some examples of 2-azapurine nucleosides. However, there is no disclosure on 7-deaza-2-azapurine nucleosides.

In Biochimica et Biophysica Acta, 520 (1978), p. 441-451, there is disclosed the enzymatic synthesis of 2-azaadenosine-5'-diphosphate and 2-aza inosine-5'-diphosphate and their polymerization to homopolymers using E.coli polynucleotide phosphorylase. This method is complex and it is not capable of producing mixed sequences. Furthermore, there was reported on the capability of the homopolymers to form double- and triple-stranded complexes with other homopolymers. Those compounds only containing 2-azaadenosine as base have proved to be UV sensitive and labile.

In J. Org. Chem. 1995, 60, 6262-6269, there is disclosed the synthesis and biophysical and biological properties of oligonucleotides containing 2-aza-2'-deoxyinosine. There is disclosure on a 2-aza inosine nucleoside, which is modified by a particular photochemically cleavable protecting group at one of the ring nitrogen atoms. However, as can be seen from table 1 on page 6266, $I^{Az}$ does not differentiate well between the natural nucleobases. As can be seen further, the stability of the base pair $I^{Az}/G$ is 13° less than the regular base pair C/G and 9° less than the base pair A/T. The replacement of C by $I^{Az}$ would therefore not be suitable for mimicking the stability of a A/T base pair.

In Liebigs Ann. Chem. 1990, 647-651, there are disclosed 2-azaadenine and a nucleoside of methylthioimidazotriazine as well as the corresponding methoxy compound. No phosphates or phosphoramidites are disclosed. Furthermore, there is no disclosure on how to prepare oligonucleotides containing 2-aza-adenosine at specific positions. Their hybridization behaviour is not disclosed. Furthermore, there is no disclosure on 2-aza-2'-deoxyadenosinetriphosphate.

The present invention is particularly useful in nucleic acid determinations, for example in analytics, especially in the field of health care. Nucleic acids have been found to be useful analytes for the determination of the presence or absence of genes or micro-organisms in human body fluids, food or environment. Nucleic acid analysis has found widespread use after the introduction of nucleic acid amplification, like the Polymerase Chain Reaction (PCR, see U.S. Pat. No. 4,683,202). Thus, sufficient amounts of nucleic acids are available from each sample. The nucleic acids can be determined from this pretreated sample using a variety of different techniques, dependent from the particular purpose. Most assays require the use of a probe which is either immobilized or immobilizable or is labelled by attachment of one or more reporter groups. A reporter group has the characteristics to be itself capable to be determined or it can be reacted with reagents that make the probe determinable via said reporter group. Thus, for example, probes that are labelled by reporter groups can be determined, as can be hybrids that contain the probe and a nucleic acid to be determined. In case of immobilized probes, the hybrid between the probe and the nucleic acid to be determined is determined at the solid phase to which the probe is bound. In a particular form of assays, not only one nucleic acid having a specific sequence, but a large number of nucleic acids of different sequence is determined. For this purpose, the probes are immobilized in tiny spots in an array on a flat surface such as a glass chip (EP-A-0 476 014 and TIBTECH (1997), Vol. 15, 465-469).

The basic principle of using oligonucleotide arrays was first proposed in the late 1980s when the concept of determining a DNA sequence by hybridization to a comprehensive set of oligonucleotides (SBH, sequencing by hybridization) was developed.

There are many proposals to include modified or non-natural heterocyclic groups instead of the natural nucleobases. Examples of such non-natural groups are 7-deaza-dGTP which, when introduced into a nucleic acid replacing dGTP reduces band compressing in sequencing gels (EP-B-0 286 028).

Nucleic acid determinations generally suffer from the problem that the base pairing possibilities between the natural bases A and T and C and G have different stability. This can be attributed to the different capability of the bases to form hydrogen bonding. Thus, the dA-dT- base pair has two hydrogen bridges, while the dG-dC- base pair has 3 hydrogen bridges. This results in different melting temperatures (Tm) of hybrids, depending on the GC content. The higher the GC content, the higher the Tm. In routine nucleic acid analysis, however, there would be the wish to equalize the Tm for nucleic acids of the same length, or even independent from the length of the nucleic acid or the binding region in order to be in the position to apply similar hybridization conditions for all assays. This is particularly necessary for assays using arrays, as on such arrays the hybridizing conditions for each probe must be identical.

One solution was the use of low hybridization temperatures. Under such conditions, many nucleic acids having a low degree of base sequence complementarity will bind to the probe. This is called unspecific binding which does not allow discrimination between similar sequences.

Another proposal was directed to the use of chemical reagents in the hybridization mixture, for example the addition of tetramethylammonium chloride (TMAC). This reagent reduces the difference between the stability of dG-dC and dA-dT basepairs but the effect is insufficient for short oligonucleotides. Further the addition of salts such as TMAC may not be wellcome as it complicates optimization of the assay.

Another proposal was directed to the use of different concentrations of each different (immobilized) probe in one assay. This was found to be technically complex if not impossible on a chip surface.

As a further option the substitution of ribonucleotides in an oligonucleotide composed of deoxyribonucleotides, and vice versa was applied for the adaptation of DNA stability, Hoheisel (1996), Nucleic Acids Res. 24, 430-432.

All proposals known now have some disadvantages. Therefore, there is still a need to provide probes the Tm of which is not very dependent from their GC content.

FIG. 1 shows how $z^2A_d$ is capable of base pairing with a dG in another strand of a nucleic acid.

In FIG. 2 there are shown different compounds of the invention, like 2-aza-2'-deoxyadenosine (2), the corresponding triphosphate (11), a phosphoramidite for the introduction of 2-aza-2'-deoxyadenosine into oligonucleotides during conventional chemical automated synthesis (10 b) and a H-phosphonate (12).

Figure 1:
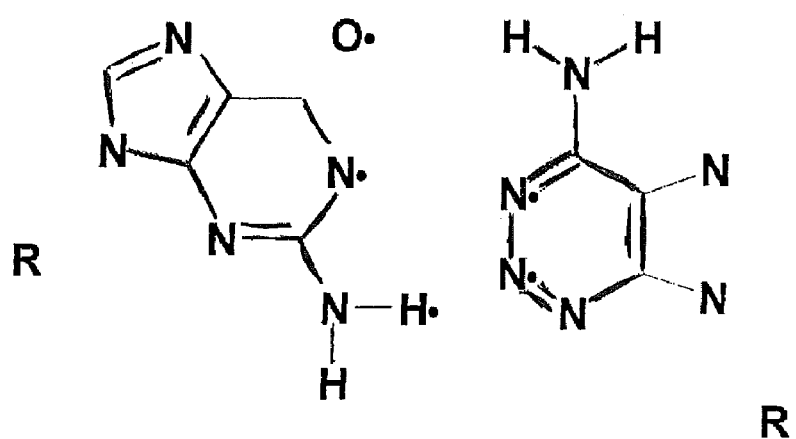
Figure 2:
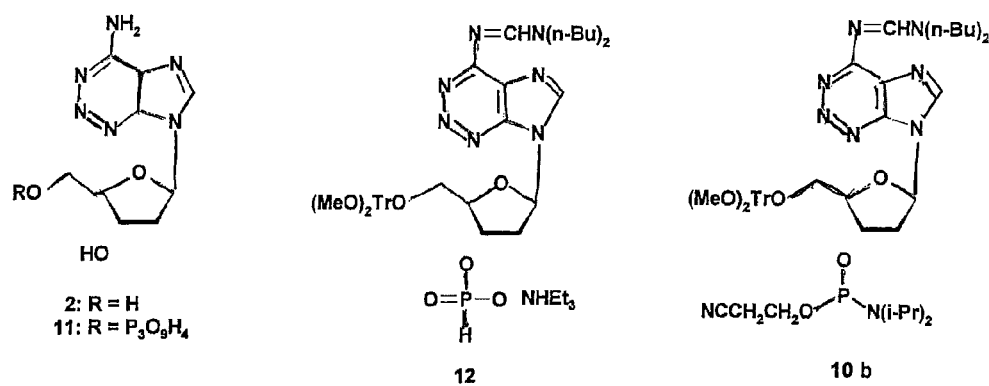
Figure 3:
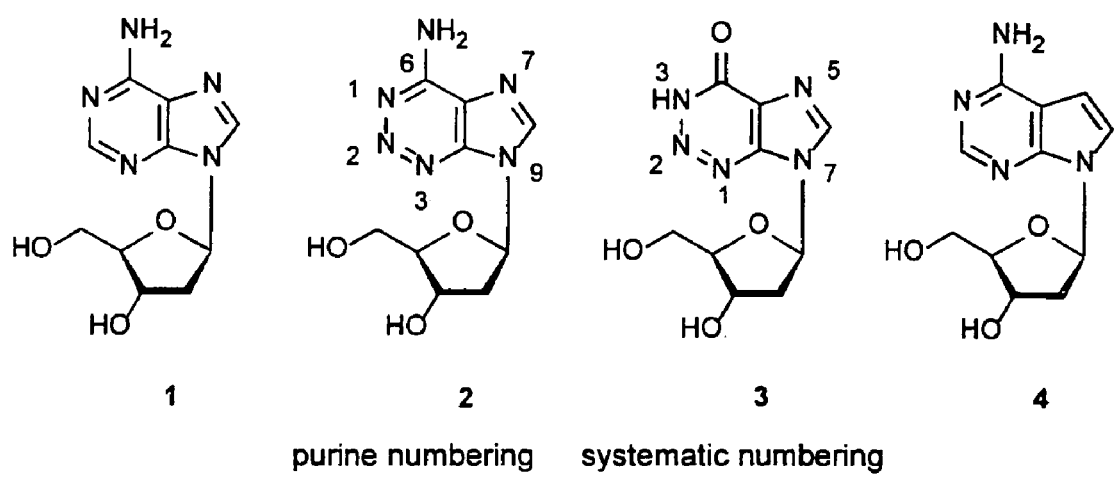
FIG. 3 shows compounds useful in the present invention. The purine numbering for compound 2 and the systematic numbering for compound 3 is given.
Figure 4:
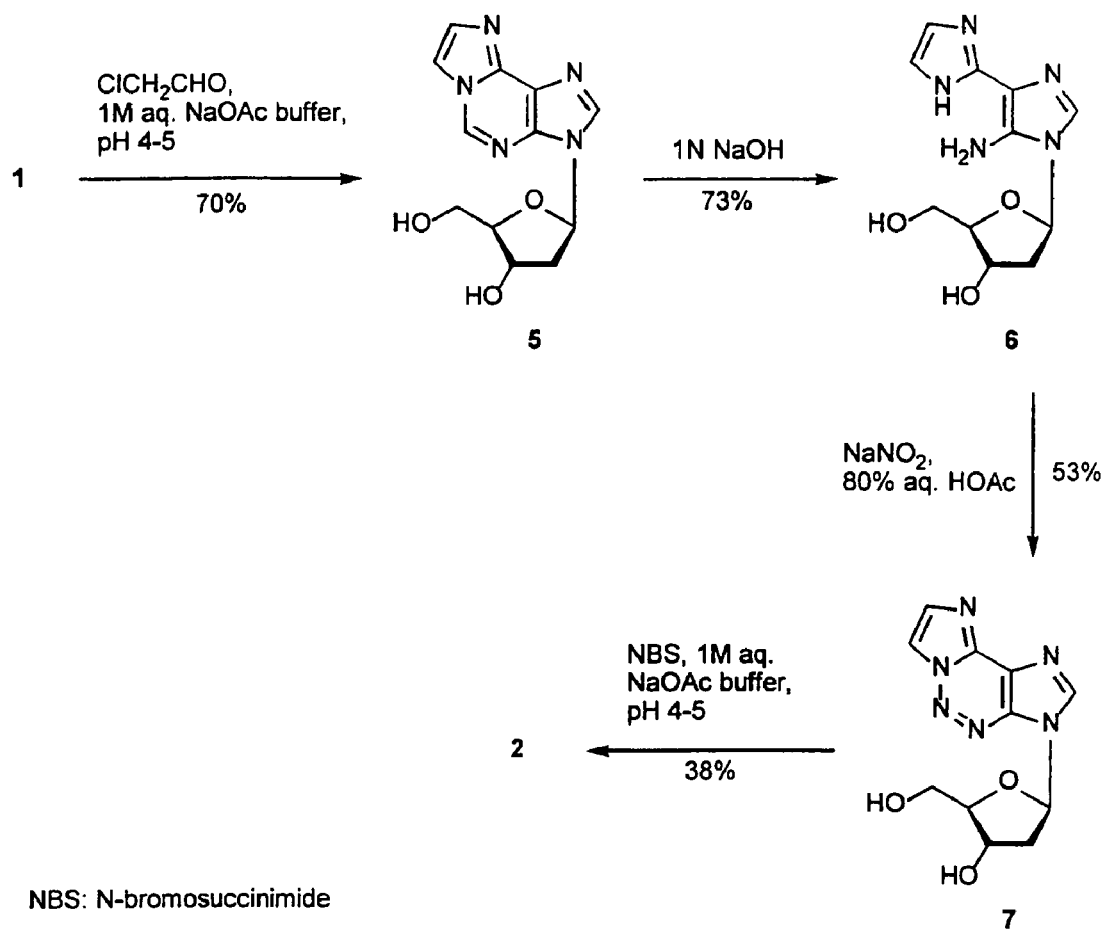
FIG. 4 shows a route for synthesis of 2-aza-2'-deoxy-adenosine.
Figure 5:
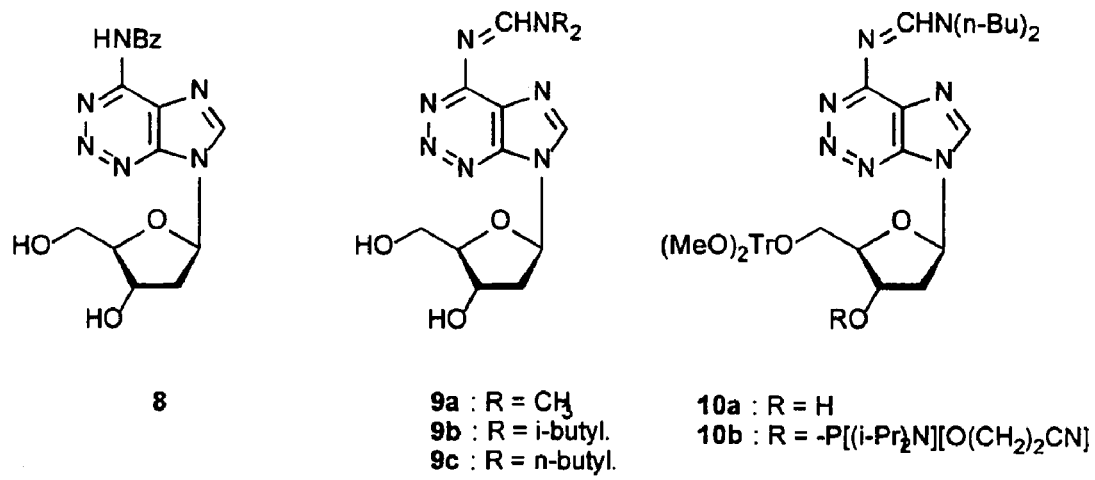
FIG. 5 shows compounds of the invention.

The subject of the present invention is a nucleic acid binding compound comprising a backbone, said backbone having attached heterocyclic groups capable of base pairing to natural nucleobases at least one of said heterocyclic groups being one of the naturally occurring nucleobases characterized in that at least one other of said heterocyclic groups is a group of the general formula I Formula I wherein W is selected independently from X, Y and Z from the group consisting of N and CR$^2$, Z is selected from the group consisting of N and C with the proviso that
  if Z is N, then
    X independently from W and Y is selected from the group consisting of N and CR$^3$, and
    Y independently from W and X is selected from the group consisting of N and CR$^4$,
    and the bond between X and Y is a double bond and the bond between Y and Z is a single bond, and
  if Z is C, then
    X is NR$^{33}$, and
    Y is selected from the group consisting of N and CR$^4$ and
    the bond between Z and Y is a double bond and the bond between X and Y is a single bond, R$^1$, R$^2$, R$^3$ and R$^4$ are independently selected from the group consisting of —H, -halogen, —OR$^{13}$, —SR$^{19}$, —(C$_1$-C$_{10}$)-alkyl, —(C$_2$-C$_{10}$)-alkenyl, —(C$_2$-C$_{10}$)-alkynyl, —NO$_2$, —NR$^5$R$^6$, -cyano, and —C(=O)R$^{11}$, R$^{11}$ is selected from the group consisting of —OH, —(C$_1$-C$_6$)-alkoxy, —(C$_6$-C$_{22}$)-aryloxy, and NHR$^{12}$, R$^5$, R$^6$, R$^{12}$, R$^{13}$, R$^{19}$ and R$^{33}$ are selected independently from the group consisting of —H, —(C$_1$-C$_{10}$)-alkyl, —(C$_2$-C$_{10}$)-alkenyl, —(C$_2$-C$_{10}$)-alkinyl, —(C$_6$-C$_{22}$)-aryl, a protecting group and a reporter group, r and s are independently of each other an integer of 1 to 18, D is the position of attachment of the group to the rest of the nucleic acid binding compound, and said alkyl, alkenyl and alkynyl being unsubstituted or substituted by one or more moieties selected from the group consisting of -halogen, —SH, —S—(C$_1$-C$_6$)-alkyl, —(C$_1$-C$_6$)-alkoxy, —OH, —NR$^5$R$^6$, —COR$^{11}$, —NH—CONR$^5$R$^6$, —NH—CSNR$^5$R$^6$ and —[O—(CH$_2$)$_r$]$_s$—NR$^5$R$^6$.

By way of example, in the following there is given an explanation of the advantageous property of the compounds of the invention by showing them at the example of 2-aza-2'-deoxyadenosine (2, $z^2A_d$) which forms specifically stable base pairs with 2'-deoxyguanosine (dG) but much less stable base pairs with 2'-deoxythymidine (dT), 2'-deoxycytidine (dC) and 2'-deoxyadenosine (dA). The new base pair ($z^2A_d$-dG) is of analogous stability as a regular dA-dT base pair.

In order to equalize Tm, in a nucleic acid binding compound one or more C in a strand complementary to a G in the nucleic acid to be determined could be replaced by a $z^2A_d$. The oligonucleotide would then bind specifically to the target sequence containing dG opposite to $z^2A_d$ but with the stability of a dA-dT and not a dG-dC base pair. This general principle of course is not limited to $z^2A_d$, as bases showing the same characteristics in the 6-membered ring would be expected to have the same properties based on the above explanation due to their containing the 2-azapurine structure. Particularly, the farer the part of the heterocyclic group from the part participating in the base pairing, the more tolerant will the oligomer be over modifications in the chemical structure, for example the attachment of groups to this part of the heterocyclic rings. In the following, when reference is made to the modified base (of the invention), there is made reference to a heterocyclic group according to general formula I.

The broken line in formula I indicates that there are several possibilities, depending upon the definitions of X, Y and Z, to localize a double bond. It is apparent to the man skilled in art that the choice of a specific definition of Z will require a double bond to be either between Z and Y or between X and Y. It is further evident that there will be not each a double bond between X and Y and Y and Z.

Halogen means a fluoro, chloro, bromo or iodo group. The most preferred halogen groups are —Cl and —Br.

Alkyl groups are preferably chosen from alkyl groups containing from 1 to 10 carbon atoms, either arranged in linear, branched or cyclic form. The actual length of the alkyl group will depend on the steric situation at the specific position where the alkyl group is located. If there are steric constraints, the alkyl group will generally be smaller, the methyl and ethyl group being most preferred. All alkyl, alkenyl and alkynyl groups can be either unsubstituted or substituted. Substitution by hetero atoms as outlined above, will help to increase solubility in aqueous solutions.

Alkenyl groups are preferably selected from alkenyl groups containing from 2 to 10 carbon atoms. For the selections similar considerations apply as for alkyl groups. They also can be linear, branched and cyclic. The most preferred alkenyl group is the ethylene group.

Alkynyl groups have preferably from 2 to 10 carbon atoms. Again, those carbon atoms can be arranged in linear, branched and cyclic manner. Further, there can be more than one triple bond in the alkynyl group. The most preferred alkynyl group is the 3-propargyl-group.

Alkoxy groups preferably contain from 1 to 6 carbon atoms and are attached to the rest of the moiety via the oxygen atom.

For the alkyl group contained in the alkoxy groups, the same considerations apply as for alkyl groups. The most preferred alkoxy group is the methoxy group.

Aryloxy groups preferably contain from 6 to 20 carbon atoms. Those carbon atoms may be contained in one or more aromatic rings and further in side chains (for example, alkyl chains) attached to the aromatic moiety. Preferred aryloxy group are the phenoxy and the benzoxy group.

Preferred O-protecting groups in $R^{14}$ are the aroyl groups, the acyl groups and the silyl groups. Among these most preferred is the benzoyl group.

Preferred silyl groups are the trialkylsilyl groups, like triethylsilyl.

Any atom in the definitions within the formulae presented herein is not limited to a specific isotope. Thus, a phosphorous atom (P) can either mean the regular $^{31}P$ or the radioactive $^{32}P$ or a mixture thereof. The same applies for hydrogen (H/D/T), carbon (C), iodine (Cl, Br, I) and nitrogen (N).

Preferred group —$NR^5R^6$ in the definition of $R^2$, $R^3$ and $R^4$ is the —$NH_2$ group. In this case, it is evident that during chemical synthesis of compounds containing such group of formula I one of the hydrogen atoms of this amino group might be protected by suitable amino protecting group. Such protecting groups are generally known to a man skilled in the art.

The same applies for the definitions of $R^1$.

During chemical synthesis, any groups —OH, —SH and —$NH_2$ (including those groups in reporter groups) should be protected by suitable protecting groups. Further, during chemical synthesis, the compound will be attached for convenience to a solid phase. In these cases, the definitions of the substituents given above will be selected accordingly.

A protecting group is a chemical group that is attached to a functional moiety (for example to the oxygen in a hydroxyl group, replacing the hydrogen) to protect the functional group from reacting in an undesired way. A protecting group is further defined by the fact that it can be removed without destroying the biological activity of the molecule formed, here the binding of the nucleic acid binding compound to a nucleic acid. Suitable protecting groups are known to a man skilled in the art. Especially preferred protecting groups for example for hydroxyl groups at the 5'-end of a nucleotide or oligonucleotide are selected from the trityl group, for example dimethoxytrityl.

Preferred protecting groups at exocyclic amino groups in formula I are the acyl groups, most preferred the benzoyl group (Bz), phenoxyacetyl or acetyl or formyl, and the N,N-dialkylformamidine group, preferentially the dimethyl-, diisobutyl-, and the di-n-butylformamidine group.

The nucleic acid binding compound according to the invention preferably has a length of less than 100 subunits, more preferably of from 10 to 30 subunits. In order to be active as nucleic acid binding compound, the substituents should be chosen such that hydrogen bonds to heterocyclic groups at the nucleic acid to be bound are enabled, preferably by Watson Crick base pairing and/or in the way as disclosed in FIG. 1. Compounds in which the substituents do not enable such preferred hydrogen bonding, can be useful as intermediates for the preparation of nucleic acid binding compounds. Preferred nucleic acid binding compounds of the invention are those which are chemically synthesized.

If the nucleic acid binding compound is to be used as a probe for the determination of a nucleic acid, or any other identification of the compound or the nucleic acid is intended, any of the substituents are selected such as to contain a reporter group. While as many reporter groups can be attached as useful to label the nucleic acid compound sufficiently, it is preferred to attach only a limited number of reporter groups to a single subunit, such that recognition of nucleic acids, affinities to nucleic acids and solubility is not affected such that the probe would not be useful in hybridization assays. In a very preferred case, there will be only from 1 to 4, most preferably 1 or 2 or most preferred only one reporter group in each nucleic acid binding compound. There are formats for the nucleic acid determination which require more than one reporter group attached to the probe. An example for such formats is disclosed in WO92/02638. In this case, one of the reporter groups will be a fluorescence emitter, while the other is a fluorescence quencher.

Reporter groups are generally groups that make the nucleic acid binding compound as well as any nucleic acids bound thereo distinguishable from the remainder of the liquid, i.e. the sample (nucleic acid binding compounds having attached a reporter group can also be termed labelled nucleic acid binding compounds, labelled probes or just probes). This distinction can be either effected by selecting the reporter group from the group of directly or indirectly detectable groups or from the groups of immobilized or immobilizable groups. Directly detectable groups are for example fluorescent compounds, like fluorescein and its derivatives, like hexachlorofluorescein and hexafluorofluorescein, rhodamines, psoralenes squaraines, porphyrines, fluorescent particles, bioluminescent compounds, like acridinium esters and luminol, or the cyanine dyes, like Cy-5. Examples of such compounds are disclosed in EP 0 680 969. Further, spin labels like TEMPO, electrochemically detectably groups, ferrocene, viologene, heavy metal chelates and electrochemiluminescent labels, like ruthenium bispyridyl complexes, and naphthoquinones, quencherdyes, like dabcyl, and nuclease active complexes, for example of Fe and Cu, are useful detectable groups. Indirectly detectable groups are groups that can be recognized by another moiety which is directly or indirectly labelled. Examples of such indirect detectable groups are for example haptens, like digoxigenin or biotin. Digoxigenin for example can be recognized by antibodies against digoxigenin. Those anibodies may either be labelled directly or can be recognized by labelled antibodies directed against the (antidigoxigenin) antibodies. Formats based on the recognition of digoxigenin are disclosed in EP-B-0 324 474. Biotin can be recognized by avidin and similar compounds, like streptavidin and other biotin binding compounds. Again, those compounds can be labelled directly or indirectly.

The reporter group can further be a nucleotide sequence which does not interfere with other nucleotide sequences in the sample. The sequence can therefore be specifically recognized by nucleotide containing a complementary sequence. This nucleotide sequence can be labelled directly or indirectly or can be immobilizable or immobilized.

A reporter group can further be a solid phase. Attachment of the nucleic acid binding compound with solid phase can be either directly or indirectly as pointed out above for the detectable group.

Direct labelling can be effected by covalent coupling of a nucleic acid binding compound to a reactive group on the solid phase, i.e. preferably via a linker. Indirect labelling can be made similar as disclosed above for the detectable groups. Preferably, indirect attachment is non-covalently by biospecific interactions, for example those selected from the group of hapten-antibody, vitamin-receptor and nucleic acid-complementary nucleic acid. Again, those interactions and their use in nucleic acid assays is known to a man skilled in the art.

Solid phases that are useful for immobilization of the probe according to the invention are preferably selected from the group of polystyrene, polyethylene, polypropylene, glass and $TiO_2$. The formats of such solid phases can be selected according to the needs of the instrumentation and format of the assay. For example, a solid phase may assume the form of a bead or a vessel.

The term reporter group and the specific embodiments preferably include a linker which is used to connect the moiety intended to be used (the actual solid phase or the fluorophoric moiety, to the position of attachment as the reporter group. The linker will provide flexibility such that the nucleic acid binding compound can bind the nucleic acid sequence to be determined without major hindrance by the solid phase. Linkers, especially those that are not hydrophobic, for example based on consecutive ethylenoxy units, for example as disclosed in DE 3943522 are known to a man skilled in the art.

From the above explanation, it becomes clear that the invention would still work, even if the backbone of the probe is not an oligonucleotide in the strict sense. There were described in the last years nucleic binding compounds that have similar properties like oligonucleotides, but differ in their backbone. The backbone is generally considered to be the part of the nucleic acid binding compound that bears the bases, mostly in linear manner, bound to identical or not identical subunits. The most popular backbone is the naturally occurring sugar phosphate backbone of nucleic acids (containing either ribonucleoside subunits (RNA), deoxyribonucleoside subunits (DNA) or peptide nucleic acid subunits (PNA)). Therefore, in a preferred embodiment, the backbone comprises sugar and phosphate moieties. In a further preferred embodiment, the sugar configuration is selected from the group consisting of the α-D-, β-D-, α-L- and β-L-configurations, most preferred the compound contains at least one 2'-deoxy-β-D-erythro-pentofuranosyl moiety or one β-D-ribofuranosyl moiety.

Preferred, D is the glycosid C-1 of a sugar moiety of the compound according to the invention. Preferred compounds of formula VI are those wherein $R^1$ is $NH_2$, W is N, Z is N, Y is C, X is N and $R^{14}$ is H.

Further preferred nucleic acid binding compounds contain at least one group of formula I, wherein $R^1$ is the group $-NR^{20}R^{21}$, which are either 2-aza-adenosine or derivatives thereof. As derivatives of 2-aza-adenine there are considered here compounds that provide hydrogen bonding via the same atoms as 2-aza-adenine to G and dG in a nucleic acid bound to the nucleic acid binding compound of the invention. The most preferred group of formula I is 2-aza-adenine, bound to the backbone via the $N^9$ atom. Those groups both discriminate clearly between the natural nucleobases and in addition provide a very similar stability as the A-T base pair.

The nucleic acid binding compound will be constructed such that it contains a nucleobase sequence which is substantially complementary to the nucleic acid to be determined or the nucleic acid to which it is intended to be bound by base pairing. As those nucleic acids will usually contain at least once any of the naturally occurring nucleobases Ade, Cyt, Gua and Thy or Ura, the nucleic acid binding compound according to the invention will also contain any of those four bases. However, according to the invention, at least one of the heterocyclic groups in a position of the nucleic acid binding compound located vis-à-vis the G in the nucleic acid to be determined as replaced by the heterocyclic base of formula I. If there is more than one G in the sequence to which the nucleic acid binding compound is intended to be hybridized on the nucleic acid, preferably as many C's in the nucleic acid binding compound are chosen to be heterocyclic groups of formula I as necessary to provide the Tm as intended.

However, the nucleic acid binding compounds of the invention display the same base pairing selectivity also versus other heterocyclic groups in the position located vis-à-vis the position of the nucleic acid binding compound at which the group of formula I is located, especially versus derivatives of G, for example $c^7G_d$, $z^8c^7G_d$ and $Z^8G_d$. In these nominations, $c^7$ means that in the 7-position there will be a carbon atom and $z^8$ will correspondingly mean that in the 8-position there will be a nitrogen atom. Further, derivatives of G that can be recognized according to the invention, are nucleobases G which are labelled by the attachment of detectable groups, and iso $G_d$.

The nucleic acid can also contain a heterocyclic group of formula I itself. The corresponding base on the nucleic acid binding compound will preferably be selected such as to base pair with this group, for example to be dG. The nucleic acid can contain natural and/or non-natural bases, for example 7-deaza-dGTP. Thus, the term nucleic acid will be construed in the present invention very broadly. Nucleic acids having mixed base sequences being preferred.

The nucleic acid binding compound according to the invention will bind to nucleic acids preferably in the antiparallel mode. However, by carefully selecting the nucleobases of a nucleic acid and/or of the nucleic binding compound, the binding can also be forced to be in the parallel mode. Parallel hybridization of nucleic acids containing iso-C and iso-G are for example disclosed in EP 0 624 161.

Preferred nucleic acid binding compounds are those, wherein the backbone comprises one or more moieties of the general formula II

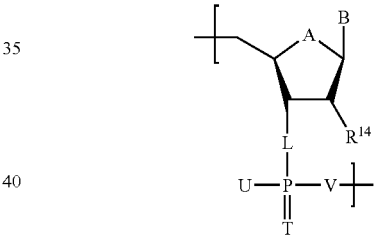

Formula II wherein

A is selected from the group consisting of O, S and $N-(C_1-C_{10})$-alkyl,

L is selected from the group consisting of oxy, sulfanediyl and $-NR^{22}-$,

T is selected from the group consisting of oxo, thioxo and selenoxo,

U is selected from the group consisting of $-OH$, $-O$-reporter group, $-SH$, $-S$ reporter group $-SeH$, $-(C_1-C_{10})$-alkoxy, $(C_1-C_{10})$-alkyl, $-(C_6-C_{22})$-aryl, $-(C_6-C_{14})$-aryl-$(C_1-C_{10})$-alkyl, $-NR^{23}R^{24}$, and $-O-(C_1-C_{10})$-alkyl-$O-(C_1-C_{10})$-alkyl-$R^{25}$, or wherein $-NR^{23}R^{24}$ can together with N be a 5-6-membered heterocyclic ring, V is selected from the group consisting of oxy, sulfanediyl or $-NR^{22}-$, $R^{14}$ is selected from the group consisting of $-H$, $-OH$, $-(C_1-C_{10})$-alkoxy, $-(C_2-C_{10})$-alkenyloxy, -halogen, -azido, $-O$-allyl, $-O$-alkinyl, and $-NH_2$, $R^{22}$ is independently selected from the group of $-H$ and $-(C_1-C_{10})$-alkyl, $R^{23}$ and $R^{24}$ are independently selected from the group consisting of $-(C_1-C_{10})$-alkyl, $-(C_1-C_{20})$-aryl, $-(C_6-$ $C_{14}$)-aryl-($C_1$-$C_{10}$)-alkyl, —($C_1$-$C_6$)-alkyl-[NH($CH_2$)$_c$]$_d$—$NR^{26}R^{27}$ and a reporter group, $R^{25}$ is selected from the group consisting of —H, —OH, -halogen, -amino, —($C_1$-$C_{18}$)-alkylamino, —COOH, —$CONH_2$ and —COO($_1$-$C_4$)-alkyl and a reporter group, $R^{26}$ and $R^{27}$ are independently selected from the group consisting from —H, —($C_1$-$C_6$)-alkyl, and —($C_1$-$C_4$)-alkoxy-($C_1$-$C_6$)-alkyl and a reporter group, c is an integer from 2 to 6, d is an integer from 0 to 6, and B is a moiety of formula I, wherein any alkyl, alkenyl and alkynyl can be substituted or unsubstituted, and any salts thereof.

The preferred definitions of the groups as defined under formula I apply to formula II and the following formulae, if not indicated otherwise.

A preferred subject of the invention is therefore a nucleic acid binding compound as outlined above, wherein the backbone comprises one or more moieties of the general formula III

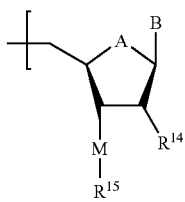

Formula III wherein

A is selected from the group consisting of O, S and N—($C_1$-$C_6$)-alkyl,

M is selected from the group consisting of oxy, sulfanediyl, —$NR^{22}$—, —($C_1$-$C_{10}$)-alkyl-, or —O—($C_1$-$C_{10}$)-alkyl-O—, and —S—($C_1$-$C_{10}$)-alkyl-)— and $NR^{22}$—($C_1$-$C_6$)-alkyl-O—, $R^{22}$ is selected from the group of —H, —($C_1$-$C_{10}$)-alkyl, a protecting group and a reporter group, $R^{14}$ is selected from the group consisting of —H, —OH, —($C_1$-$C_{10}$)-alkoxy, —($C_2$-$C_{10}$)-alkenyloxy, —($C_2$-$C_{10}$)-alkynyloxy, -halogen, -azido, SH, —($C_1$-$C_{10}$)-alkylmercapto and —$NH_2$, $R^{15}$ is selected from the group consisting of —H, —($C_1$-$C_6$)-alkyl, —($C_2$-$C_{10}$)-alkenyl, —($C_2$-$C_{10}$)-alkynyl, —($C_2$-$C_{10}$)-alkyl-carbonyl, —($C_3$-$C_{19}$)-alkenyl-carbonyl, —($C_3$-$C_{19}$)-alkynyl-carbonyl, —($C_6$-$C_{14}$)-aryl-($C_1$-$C_{10}$)-alkyl, a solid phase and a group of formula IV

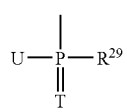

Formula IV wherein

T is selected from the group consisting of oxo, thioxo and selenoxo, and

U is selected from the group consisting of —OH, —O-reporter group, —SH, —SeH, —($C_1$-$C_{10}$)-alkoxy, —($C_1$-$C_{10}$)-alkyl, —($C_6$-$C_{22}$)-aryl, —($C_6$-$C_{14}$)-aryl-($C_1$-$C_{10}$)-alkyl, —$NR^{23}R^{24}$, and —O—($C_1$-$C_{10}$)-alkyl-O—($C_1$-$C_{10}$)-alkyl-$R^{25}$, or wherein $NR^{23}R^{24}$ can together with N be a 5-6-membered heterocyclic ring, $R^{23}$ and $R^{24}$ are independently selected from the group consisting of —($C_1$-$C_{10}$)-alkyl, —$C_1$-$C_{20}$)-aryl, —($C_6$-$C_{14}$)-aryl-($C_1$-$C_{10}$)-alkyl, —($C_1$-$C_6$)-alkyl-[NH($CH_2$)$_c$]$_d$—$NR^{26}R^{27}$, $R^{25}$ is selected from the group consisting of —H, —OH, -halogen, -amino, —($C_1$-$C_{18}$)-alkylamino, —COOH, —$CONH_2$ and —COO($C_1$-$C_4$)-alkyl, $R^{26}$ and $R^{27}$ are independently selected from the group consisting from —H, —($C_1$-$C_6$)-alkyl, and —($C_1$-$C_4$)-alkoxy-($C_1$-$C_6$)-alkyl $R^{29}$ is selected from the group consisting of —$OR^{30}$ and —$SR^{30}$, $R^{30}$ is selected from the group consisting of —H, —($C_1$-$C_{10}$)-alkyl, —($C_2$-$C_{10}$)-alkenyl, —($C_6$-$C_{22}$)-aryl, a protecting group, a solid phase and a reporter group B is the link to a moiety of formula I, and any salts thereof.

For the definitions and preferences the particulars apply as outlined for the substituents under formulae I and II, if not specified otherwise specifically for formula III.

Preferably, in compounds of formula II, $R^{14}$ is hydrogen. Preferred definition of L is oxy. Preferred definition of U is —OH and —O-reporter group. Preferred definition of V is oxy. Preferred definition of c is an integer from 2 to 4, and of d an interger from 0 to 2.

Compounds of formula II are especially suited to contain the heterocyclic moiety of the invention as an integrated part (preferably not at one of the termini) of the nucleic acid binding compound.

The group $NR^{23}R^{24}$ is preferably selected from the group consisting of dialkylamino groups. In case of this group together with the forming of 5- or 6-membered heterocyclic ring, it assumes preferably the definition of pyrrolidinyl or piperidinyl.

Preferred aryl group is the phenyl or naphtyl moiety, either unsubstituted or substituted by one or more of amino, -aminoalkyl, —O—($C_1$-$C_{10}$)-alkyl, —S—($C_1$-$C_{10}$)-alkyl, —($C_1$-$C_{10}$)-alkyl, sulfonyl, sulfenyl, sulfinyl, nitro and nitroso. Most preferred aryl group is the phenyl group. Preferred arylalkyl group is the benzyl group. The preferred alkylamino group is the ethylamino group. The preferred —COO($C_1$-$C_4$) alkyl group contains one or two carbon atoms in the alkyl moiety (methyl or ethyl esters).

Nucleic acid binding compounds, wherein the group of formula I is attached to submit, for example the nucleotide, at the 3'-terminus of the compound, are useful either as starting compound for longer compounds or/and as end-labelled probes. This group of compounds is especially preferred because the terminal position of probes generally is the most tolerant in view of attachment of chemical moieties.

A preferred subject of the invention is a nucleic acid binding compound as outlined above comprising a backbone moiety of the formula V

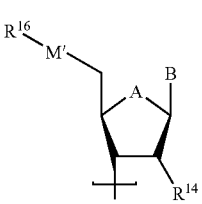

Formula V wherein
A is selected from the group consisting of O, S and N—($C_1$-$C_6$)-alkyl,
M' is selected from the group consisting of oxy, sulfanediyl, —$NR^{22}$—, —($C_1$-$C_{10}$)-alkyl, or —O—($C_1$-$C_{10}$)-alkyl-O—, and —S—($C_1$-$C_{10}$)-alkyl-O— and —$NR^{22}$—($C_1$-$C_6$)-alkyl-O—,
$R^{22}$ is selected from the group of —H, a protecting group, a reporter group and —($C_1$-$C_{10}$)-alkyl,
$R^{14}$ is selected from the group consisting of —H, —OH, —($C_1$-$C_{10}$)-alkoxy, —($C_2$-$C_{10}$)-alkenyloxy, —($C_2$-$C_{10}$)-alkynyloxy, -halogen, azido, —SH, —S—($C_1$-$C_6$)-alkylmercapto and $NH_2$,
$R^{16}$ is selected from the group consisting of —H, —($C_1$-$C_8$)-alkyl, —($C_2$-$C_{18}$)-alkenyl, —($C_2$-$C_8$)-alkynyl, —($C_2$-$C_8$)-alkyl-carbonyl, —($C_3$-$C_{19}$)-alkenyl-carbonyl, —($C_3$-$C_{19}$)-alkynyl-arbonyl, —($C_6$-$C_{14}$)-aryl-($C_1$-$C_8$)-alkyl, a protective group or a compound of formula IV

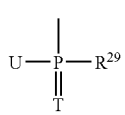

Formula IV wherein
T is selected from the group consisting of oxo, thioxo and selenoxo,
U is selected from the group consisting of —OH, —SH, —SeH, —($C_1$-$C_{10}$)-alkoxy, —($C_1$-$C_{10}$)-alkyl, —($C_6$-$C_{22}$)-aryl, —($C_6$-$C_{14}$)-aryl-($C_1$-$C_{10}$)-alkyl, —$NR^{23}R^{24}$, and —O—($C_1$-$C_{10}$)-alkyl-O—($C_1$-$C_{10}$)-alkyl-$R^{25}$, wherein $NR^{23}R^{24}$ can together with N be a 5-6-membered heterocyclic ring,
$R^{23}$ and $R^{24}$ are independently selected from the group consisting of —($C_1$-$C_{10}$)-alkyl, —($C_1$-$C_{20}$)-aryl, —($C_6$-$C_{14}$)-aryl-($C_1$-$C_{10}$)-alkyl, —($C_1$-$C_6$)-alkyl-[NH($CH_2$)$_c$]$_d$—$NR^{26}R^{27}$,
$R^{25}$ is selected from the group consisting of —H, —OH, -halogen, -amino, —($C_1$-$C_{18}$)-alkylamino, —COOH, —$CONH_2$ and —COO($C_1$-$C_4$)-alkyl,
$R^{26}$ and $R^{27}$ are independently selected from the group consisting from —H, —($C_1$-$C_6$)-alkyl, and —($C_1$-$C_4$)-alkoxy-($C_1$-$C_6$)-alkyl
$R^{29}$ is selected from the group consisting of —$OR^{30}$ and —$SR^{30}$,
$R^{30}$ is selected from the group consisting of —H, —($C_1$-$C_{10}$)-alkyl, —($C_2$-$C_{10}$)-alkenyl, —($C_6$-$C_{22}$)-aryl, a protecting group, a solid phase and a reporter group, and
B is the link to a moiety of formula I,
wherein any alkyl, alkenyl and alkynyl can be substituted or unsubstituted,
and any salts thereof.

Those compounds are compounds that can be used as 5'-terminally labelled probes. Regarding the definitions of the substituents, the definitions as given above apply if not indicated otherwise.

A very preferred compound is a compound of formula V, wherein M is O, $R^{16}$ is H and $R^{14}$ is selected from the group consisting of hydrogen and hydroxyl.

The backbone of the nucleic acid binding compound has the function to bear the base pairing heterocycles such that the compound can bind to a nucleic acid having a complementary sequence. Preferably, the degree of complementarity in the naturally occurring bases will be in the range from 70% up to 100% in a stretch of bases in a region effecting binding, compared to the stretch of same length in the region of the nucleic acid to be bound. Deletions and insertions of subunits in each sequence will therefor, in this calculation, be counted as gaps until the next fitting base and thus reduce complementarity by as many bases as the gap contains.

Preferred backbone contains sugar-phosphate moieties. From these, deoxy sugar containing backbones are further preferred.

Each moiety in the backbone bearing a moiety capable of base pairing to a nucleic acid of complementary sequence, including the moieties of the invention, are termed a subunit. Compounds are known that have backbones mixed of different kinds of subunits. Recently, a new kind of non-natural nucleic acid binding compounds was described. They are termed Peptide Nucleic Acids (PNA), as they contain at least one peptide bond between the subunits (WO 92/20702). The nucleic acid binding compound of the present invention can have any length. However, due to the convenience of chemical synthesis, compounds of a length of less than 100, more preferably from 10 to 30 subunits, for example nucleosides, are preferred.

The nucleic acid binding compound of the present invention can be prepared analogous to known methods.

In a first option which is particularly suitable for short compounds, the compounds are produced by chemical synthesis (multistep oligomerisation) using chemically activated derivatives of the subunits (monomers), at least one of them containing the modified base of the invention. Preferably, reactive groups in the monomers that are not involved in the actual reaction step of the oligomerisation reaction are protected using an appropriate protecting group. Such protecting groups are well known in the art and there will be no major change in protection and synthesis strategy if the groups of the invention are used.

An activated subunit is a subunit containing a substituent especially suited for chemical reaction with a predetermined substituent in another subunit, on the surface of a solid phase or in an oligomer formed of subunits. Such especially suited subunits are preferably selected from the group consisting of phosphoramidites, phosphonates (like methylphosphonates), phosphotriesters, phosphothioates, phosphodithioates, boranophosphates (see Chem. Commun. 1999, 1517-1518), phosphate methyl esters, phenylphosphonates and phosphate ethyl esters.

The predetermined substituents are preferably selected from the group of —$NH_2$, —SH and —OH.

A further subject of the invention is therefore a method for the chemical synthesis of a compound of any of claims 1 to 13 using activated subunits, wherein said subunit contains at least one group of formula I. There are several approaches known for the chemical synthesis, such as the phosphotriester method of Narang et al., Meth. Enzymol. 68, 90-99 (1979); the phosphodiester method of Brown et al., Meth. Enzymol. 68, 109-151 (1979); the diethylphosphoramidite method of Beaucage et al., Tetrahedron Lett. 22, 1859-1862 (1981); and the solid support method described in the U.S. Pat. No. 4,458,066 and in Methods in Molecular Biology, Ed. S. Agrawal, Vol. 20, Humana Press, Totowa, N.J., 1993. The most preferred method of chemical synthesis uses the phosphoramidite approach. A particularly preferred method uses a activated subunit one or more compounds of general formula VII. This method has the advantage that it is very convenient and the reagents necessary, for example a phosphoramidite containing a group of formula I, is possible to be included easily.

A further subject of the invention are therefore compounds of the general formula VII

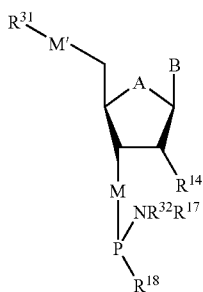

Formula VII wherein
A is selected from the group consisting of O, S and N—$(C_1-C_6)$-alkyl,
M and M' are independently selected from the group consisting of oxy, sulfanediyl, —$NR^{22}$, —$(C_1-C_{10})$-alkyl, or —O—$(C_1-C_{10})$-alkyl-O—, and —S—$(C_1-C_{10})$-alkyl-O— and —$NR^{22}$—$(C_1-C_6)$-alkyl-O—,
$R^{22}$ is selected from the group of —H and —$(C_1-C_{10})$-alkyl,
$R^{14}$ is selected from the group consisting of —H, —$OR^{31}$, —$(C_1-C_{10})$-alkoxy, —$(C_2-C_{10})$-alkenyloxy, —$(C_2-C_{10})$-alkynyloxy, -halogen, -azido $NHR^{31}$, $SR^{31}$ and —$NH_2$,
$R^{31}$ is a protecting group or a reporter group,
$R^{32}$ and $R^{17}$ are independently selected from the group consisting of —H, —$(C_1-C_{10})$-alkyl, —$(C_2-C_{10})$-alkenyl and —$(C_6-C_{22})$-aryl,
$R^{18}$ is selected from the group consisting of substituted or unsubstituted —$(C_1-C_6)$-alkyl, unsubstituted —$(C_1-C_6)$-alkoxy or —$(C_1-C_6)$-alkoxy substituted one or more times by a group selected from the group consisting of -halogen, p-nitroaryloxy and -cyano, and
B is a group of formula I.

Preferred compounds of formula VII are those wherein the group of formula I is not 2-aza-hypoxanthine. In a preferred embodiment, the group of formula I in formula VII contains at least one reporter group. Most preferable, the group of formula I contains exactly one reporter group.

Most preferred in such compounds, in —$NR^5R^6$ at least one of $R^5$ and $R^6$ is a protecting group.

Further subject of the invention are compounds of general formula IX

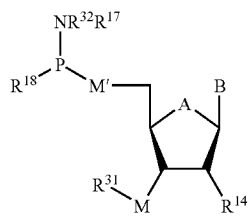

Formula IX wherein
A is selected from the group consisting of O, S and N—$(C_1-C_6)$-alkyl,
M and M' are independently selected from the group consisting of oxy, sulfanedyl, —$NR^{22}$, —$(C_1-C_{10})$-alkyl, or —O—$(C_1-C_{10})$-alkyl-O—, and —S—$(C_1-C_{10})$-alkyl-O— and —$NR^{22}$—$(C_1-C_6)$-alkyl-O—,
$R^{22}$ is selected from the group of —H and —$(C_1-C_{10})$-alkyl,
$R^{14}$ is selected from the group consisting of —H, —$OR^{31}$, —$(C_1-C_{10})$-alkoxy, —$(C_2-C_{10})$-alkenyloxy, —$(C_2-C_{10})$-alkynyloxy, -halogen, -azido $NHR^{31}$, $SR^{31}$ and —$NH_2$,
$R^{31}$ is a protecting group or a reporter group,
$R^{32}$ and $R^{17}$ are independently selected from the group consisting of —H, —$(C_1-C_{10})$-alkyl, —$(C_2-C_{10})$-alkenyl and —$(C_6-C_{22})$-aryl,
$R^{18}$ is selected from the group consisting of substituted or unsubstituted —$(C_1-C_6)$-alkyl, unsubstituted —$(C_1-C_6)$-alkoxy or —$(C_1-C_6)$-alkoxy substituted one or more times by a group selected from the group consisting of -halogen, p-nitroaryloxy and -cyano, and
B is a group of formula I

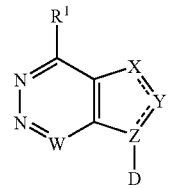

Formula I wherein
W is selected independently from X, Y and Z from the group consisting of N and $CR^2$,
Z is selected from the group consisting of N and C with the proviso that
if Z is N, then
    X independently from W and Y is selected from the group consisting of N and $CR^3$, and
    Y independently from W and X is selected from the group consisting of N and $CR^4$,
    and the bond between X and Y is a double bond and the bond between Y and Z is a single bond, and
if Z is C, then
    X is $NR^{33}$, and
    Y is selected from the group consisting of N and $CR^4$ and
    the bond between Z and Y is a double bond and the bond between X and Y is a single bond,
$R^1$, $R^2$, $R^3$ and $R^4$ are independently selected from the group consisting of —H, -halogen, —$OR^{13}$, —$SR^{19}$, —$(C_1-C_{10})$-alkyl, —$(C_2-C_{10})$-alkenyl, —$(C_2-C_{10})$-alkynyl, —$NO_2$, —$NR^5R^6$, -cyano, and —C(=O)$R^{11}$,
$R^{11}$ is selected from the group consisting of —OH, —$(C_1-C_6)$-alkoxy, —$(C_6-C_{22})$-aryloxy, and $NHR^{12}$,
$R^5$, $R^6$, $R^{12}$, $R^{13}$, $R^{19}$ and $R^{33}$ are selected independently from the group consisting of —H, —$(C_1-C_{10})$-alkyl, —$(C_2-C_{10})$-alkenyl, —$(C_2-C_{10})$-alkinyl, —$(C_6-C_{22})$-aryl, a protecting group and a reporter group,
r and s are independently of each other an integer of 1 to 18,
D is the position of attachment of the group to the rest of the nucleic acid binding compound, and
alkyl, alkenyl and alkynyl being unsubstituted or substituted by one or more moieties selected from the group consisting of -halogen, —S—$(C_1-C_6)$-alkyl, —$(C_1-C_6)$-alkoxy, —$NR^5R^6$, —CO—$R^{11}$, —NH—CO—$NR^5R^6$, —NH—$CSNR^5R^6$— and —[O—$(CH_2)_r]_s$—$_{NR}$$^5R^6$, with the proviso that at least one of $R^5$ and $R^6$ of $-NR^5R^6$ is a protecting group.

Those compounds can be used like those of formula VII in chemical synthesis.

A further subject of the invention are compounds of general formula X

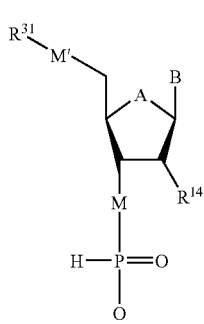

Formula X wherein

M and M' are independently selected from the group consisting of oxy, sulfanediyl, $-NR^{22}$, $-(C_1-C_{10})$-alkyl, or $-O-(C_1-C_{10})$-alkyl-O—, and $-S-(C_1-C_{10})$-alkyl-O— and $-NR^{22}-(C_1-C_6)$-alkyl-O—, $R^{22}$ is selected from the group of —H and $-(C_1-C_{10})$-alkyl, $R^{14}$ is selected from the group consisting of —H, $-OR^{31}$, $-(C_1-C_{10})$-alkoxy, $-(C_2-C_{10})$-alkenyloxy, $-(C_2-C_{10})$-alkynyloxy, -halogen, -azido $NHR^{31}$, $SR^{31}$ and $-NH_2$, $R^{31}$ is a protecting group or a reporter group, B is a group of formula I

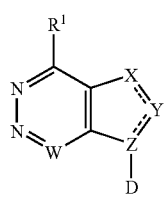

Formula I wherein

W is selected independently from X, Y and Z from the group consisting of N and $CR^2$, Z is selected from the group consisting of N and C with the proviso that if Z is N, then X independently from W and Y is selected from the group consisting of N and $CR^3$, and Y independently from W and X is selected from the group consisting of N and $CR^4$, and the bond between X and Y is a double bond and the bond between Y and Z is a single bond, and if Z is C, then X is $NR^{33}$, and Y is selected from the group consisting of N and $CR^4$ and the bond between Z and Y is a double bond and the bond between X and Y is a single bond, $R^1$, $R^2$, $R^3$ and $R^4$ are independently selected from the group consisting of —H, -halogen, $-OR^{13}$, $-SR^{19}$, $-(C_1-C_{10})$-alkyl, $-(C_2-C_{10})$-alkenyl, $-(C_2-C_{10})$-alkynyl, $-NO_2$, $-NR^5R^6$, -cyano, and $-C(=O)R^{11}$, $R^{11}$ is selected from the group consisting of —OH, $-(C_1-C_6)$-alkoxy, $-(C_6-C_{22})$-aryloxy, and $NHR^{12}$, $R^5$, $R^6$, $R^{12}$, $R^{13}$, $R^{19}$ and $R^{33}$ are selected independently from the group consisting of —H, $-(C_1-C_{10})$-alkyl, $-(C_2-C_{10})$-alkenyl, $-(C_2-C_{10})$-alkinyl, $-(C_6-C_{22})$-aryl, a protecting group and a reporter group, r and s are independently of each other an integer of 1 to 18, D is the position of attachment of the group to the rest of the nucleic acid binding compound, and alkyl, alkenyl and alkynyl being unsubstituted or substituted by one or more moieties selected from the group consisting of -halogen, $-S-(C_1-C_6)$-alkyl, $-(C_1-C_6)$-alkoxy, $-NR^5R^6$, $-CO-R^{11}$, $-NH-CO-NR^5R^6$, $-NH-CSNR^5R^6-$ and $-[O-(CH_2)_r]_s-NR^5R^6$.

Those compounds are also useful in chemical synthesis.

In another option which is more suited for long oligomers and those based on natural backbones, the oligomers are produced enzymatically. In this case, a starting oligomer is reacted with a polymerase and a triphosphate or modified triphosphate such that a monophosphate or a modified monophosphate is attached to a terminus of the oligomer, thus elongating the oligomer. Also for this method, the man skilled in the art will know several possible formates, like the nick-translation approach, or the simple primer extension (J. Sambrook. E. F. Fritsch, T. Maniatis, Molecular Cloning—A laboratory Manual, Cold Spring Harbor Laboratory Press 1989).

For example, the incorporation of $z^2A_d$ into a DNA sequence can be performed via conventional methods, e.g. by polymerase-catalyzed incorporation of $Z^2A_d$-5'-triphosphate (11).

A further subject of the invention is therefore a method for the enzymatic synthesis of a nucleic acid binding compound according to the invention comprising reacting a triphosphate subunit with a primer using a nucleic acid as a template for the elongation of the primer, wherein the triphosphate subunit contains a heterocyclic group of formula I. Preferably, the triphosphate subunit has the formula VI.

A further subject of the present invention are therefore compounds of the general formula VI

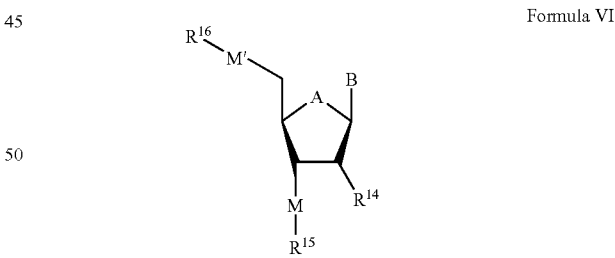

Formula VI wherein

A is selected from the group consisting of O, S and $N-(C_1-C_6)$-alkyl, $R^{14}$ is selected from the group consisting of —H, —OH, $-(C_1-C_{10})$-alkoxy, O-protecting group, S-protecting group, NH-protecting group, $-(C_2-C_{10})$-alkenyloxy, -halogen, -azido, —SH, $-(C_1-C_6)$-alkylmercapto and $-NH_2$, $R^{15}$ and $R^{16}$ are independently selected from the group consisting of —H, $-(C_1-C_8)$-alkyl, $-(C_2-C_{18})$-alkenyl, $-(C_2-C_{18})$-alkynyl, $-(C_2-C_{18})$-alkyl-carbonyl, $-(C_3-C_{19})$-alkenyl-carbonyl, $-(C_3-C_{19})$-alkynyl-carbonyl, —($C_6$-$C_{14}$)-aryl-($C_1$-$C_8$)-alkyl, a protecting group or a compound of formula IV

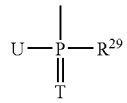

Formula IV wherein

T is selected from the group consisting of oxo, thioxo and selenoxo,

U is selected from the group consisting of —OH, —SH, —SeH, —($C_1$-$C_{10}$)-alkoxy, —($C_1$-$C_{10}$)-alkyl, —($C_6$-$C_{22}$)-aryl, —($C_6$-$C_{14}$)-aryl-($C_1$-$C_{10}$)-alkyl, —$NR^{23}R^{24}$, and —O—($C_1$-$C_{10}$)-alkyl-O—($C_1$-$C_{10}$)-alkyl-$R^{25}$, or wherein $NR^{23}R^{24}$ can together with N be a 5-6-membered heterocyclic ring, $R^{23}$ and $R^{24}$ are independently selected from the group consisting of —($C_1$-$C_{10}$)-alkyl, —($C_1$-$C_{20}$)-aryl, —($C_6$-$C_{14}$)-aryl-($C_1$-$C_{10}$)-alkyl, —($C_1$-$C_6$)-alkyl-[NH($CH_2$)$_c$]$_d$—$NR^{26}R^{27}$, $R^{25}$ is selected from the group consisting of —H, —OH, -halogen, amino, —($C_1$-$C_{18}$)-alkylamino, —COOH, —$CONH_2$ and COO($C_1$-$C_4$)-alkyl, $R^{26}$ and $R^{27}$ are independently selected from the group consisting from —H, —($C_1$-$C_6$)-alkyl, and —($C_1$-$C_4$)-alkoxy-($C_1$-$C_6$)-alkyl, $R^{29}$ is selected from the group consisting of —$OR^{30}$ and —$SR^{30}$, $R^{30}$ is selected from the group consisting of —H, —($C_1$-$C_{10}$)-alkyl, —($C_2$-$C_{10}$)-alkenyl, —($C_6$-$C_{22}$)-aryl, a protecting group, a diphosphate and a reporter group, and M and M' are independently selected from the group consisting of oxy, sulfanediyl, —$NR^{22}$, —($C_1$-$C_{10}$)-alkyl, or —O—($C_1$-$C_{10}$)-alkyl-O—, and —S—($C_1$-$C_{10}$)-alkyl-O— and —$NR^{22}$—($C_1$-$C_6$)-alkyl-O—, $R^{22}$ is selected from the group of —H and —($C_1$-$C_{10}$)-alkyl, and B is a moiety of formula I, wherein any alkyl, alkenyl and alkynyl can be substituted or unsubstituted, and wherein at least one of $R^{15}$ and $R^{16}$ is not a group of formula IV with the proviso that $MR^{16}$, $MR^{15}$ and $R^{14}$ are not each —OH if $R^1$ is —$NH_2$ and if either W and X and Y and Z is N, or W and X and Z is N and Y is $CR^4$, or W and Y and Z is N and X is $CR^3$.

Most preferred in these compounds -$MR^{16}$ is a triphosphate group and -$MR^{15}$ is OH. The most preferred compound is the one in which $R^{14}$ is —OH.

Those compounds are especially the compounds, wherein the heterocyclic moiety of the invention is contained not at the terminal position of the nucleic acid binding compound.

Preferred compounds are those, wherein M is oxy or sulfanediyl, $R^{16}$ is a compound of formula IV wherein U is —OH, T is oxo or thioxo, $R^{29}$ is —$OR^{30}$ and $R^{30}$ is a disphosphate group and the salts thereof.

Most preferred compounds are of formula VIII

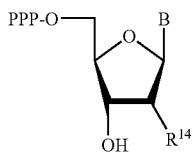

Formula VIII wherein

PPP is a triphosphate group, $R^{14}$ is selected from the group consisting of —H, —OH, —($C_1$-$C_{10}$)-alkoxy, —($C_2$-$C_{10}$)-alkenyloxy, —($C_2$-$C_{10}$)-alkynyloxy halogen, -azido and $NH_2$, and B is a group of formula I, with the proviso that $R^{14}$ is not OH if B is 2-azaadenine.

In another preferred embodiment, the group of formula I in compounds of formula VII is selected from the group consisting of groups of formula I, wherein either W is N, Z is N, Y is N and X is $CR^3$, or W is N, Z is C, Y is N and X is $CR^3$, or W is N, Z is N, Y is N and X is N.

A further subject of the invention is a method for the enzymatic synthesis of a nucleic acid binding compound of the invention comprising reacting a triphosphate subunit with a primer using a nucleic acid template for the elongation of the primer, wherein the triphosphate subunit contains a heterocyclic group of formula I.

More preferable, this method uses as a triphosphate subunit a compound of formula VIII as defined above.

The compounds of general formulae VI, VII and VIII can be prepared from compounds readily available. In a first embodiment, the compounds of formula VI characterized by the fact that the atom in the 2-position (purine numbering) are prepared by choosing the corresponding compound having a carbon atom in this position (preferably wherein $MR^{15}$ is OH and $M'R^{16}$ is OH and $R^1$ is $NH_2$, reacting it with 2-chloroacetaldehyde, cleaving the pyrimidine ring using alkaline conditions and again closing the ring using sodium nitrite and thereafter hydrolyzing the imidazole ring introduced by the aldehyde. This reaction yields a replacement of the carbon atom of the 2-position by a nitrogen atom.

This compound can then be reacted with reagents to attach protecting groups or/and activating groups, like phosphoramidites or phosphates, to the hydroxyl groups intended to be used in oligomerization. Methods for attaching protecting groups, like the dimethoxytrityl group are generally known to a man skilled in the art. Also the attachment of mono-, di- and triphosphate groups are known in the art.

In a preferred embodiment, the method for the preparation of a compound of formula VII, wherein $R^1$ is a protected amino group, $M'R^{31}$ is O-protecting group and $MPR^{18}NR^{32}R^{17}$ is O-phosphoramidite group, a compound of formula VI, wherein $M'R^{16}$ and $MR^{15}$ are each OH and $R^1$ is $NH_2$ is subjected to conditions to protect the amino group, preferably by the protecting group dialkylaminomethylidene, then reacted with reagents to protect the 5'-hydroxyl group and then reacted with an activated phosphane to produce the phosphoramidite. The resulting compound of formula VII can be used in the chemical synthesis for the introduction of the 2-aza-purine directly. The protecting group at $R^1$ will be removed during the chemical synthesis.

For an alternative synthesis of 2-aza-2'-deoxyadenosine see N. Yamaji, M. Kato, *Chemistry Lett.* 1975, 311-314).

By the above methods, it is principally possible to introduce only one monomer containing the moiety of the invention, but also more that one, as the case may be. The highest reduction of $T_m$ will occur, if all C in the binding region are replaced. This allows fine tuning of the Tm. Of course there may also be remaining Cs in any regions that are not intended to base pair with the nucleic acid to be determined.

Compounds of formula I bis VIII, in which any of substituents $R^1$, $R^2$, $R^3$ and $R^4$ are selected from the group consisting of halogen, especially Cl, cyano or $SR^{19}$ are useful as intermediate products for the synthesis of compounds wherein those substituents are selected from the group of —$NR^5R^6$ and —$OR^{13}$, preferably —$NR^5R^6$. The intermediate products can be converted into the final products by substitution reaction.

A further subject of the invention is a method for the determination of a nucleic acid comprising the steps
providing a sample suspected to contain said nucleic acid,
providing a nucleic acid binding compound of claim 1, which is essentially complementary to a part or all of said nucleic acid,
contacting said sample with said nucleic acid binding compound under conditions for binding said nucleic acid binding compound to said nucleic acid,
determining the binding product formed from said nucleic acid and said nucleic acid binding compound as a measure of the presence of said nucleic acid.

Methods for the determination of nucleic acids by hybridization are generally known in the art, for example from Sambrook et al. (cited above). They can easily be adopted to the use of the probes of the present invention. Preferably, the nucleic acid binding compound will be bound to the nucleic acid in solution, as the reaction is faster than on a solid phase. It is apparent to a man skilled in the art how to determine the Tm of the hybrid of the nucleic acid to be determined and the probe prior to the construction of an assay and its general outset. If determined once, it should be clear to the man that he should choose similar conditions in each assay using the same analyte nucleic acid.

Such determination will start with providing a sample which is suspected to contain the nucleic acid to be determined. The sample may have been subject to steps for bringing the nucleic acids in an appropriate form, for example by lysing any cells, in which the nucleic acids may be contained and would otherwise not be possible to be determined.

Further, any steps to provide the sample could contain steps to purify the nucleic acids to be determined from components of an original sample that could affect the determination. Such components could be enzymes that would, if a nucleic acid is set free from cells, would digest or degrade the nucleic acid, for example RNases. It is further preferred to also remove from the nucleic acids components of the original sample that could affect amplification of the nucleic acids.

There are several possibilities for methods for the determination of nucleic acids using the nucleic acid binding compound of the invention. In a first group, the nucleic acid binding compound is used as a detectable probe. In this case, the nucleic acid binding compound will contain a detectable reporter group. Any hybrids formed from the nucleic acid binding compound and a nucleic acid can then be determined via the detectable reporter group. This group of assays can further be devided into two groups, one being the group of homogeneous assays and the other being the heterogeneous assays. In heterogeneous assays, preferably the hybrid (binding product) will be determined when bound to a solid phase. This embodiment has the advantage that any excess of probe and other components can be removed easily from the hybrid, thus make the determination easier. The hybrid formed can be captured to a solid phase either covalently, noncovalently, specifically or unspecifically. There are several embodiments which are known to a man skilled in the art.

In the so-called homogeneous assays, the hybrid formed will not be bound to a solid phase, but will be determined either directly or indirectly in solution. A preferred example of such assays is disclosed in PCT/US 91/05571 which is incorporated by reference here. The nucleic acid binding compound of the invention is especially useful as a probe in this assay. As the assay disclosed therein may need fine tuning of melting temperatures of the primers and probes used in these assays, the present invention using the modulation of a melting temperature of the hybrid formed by the nucleic acid to be determined or the amplificates thereof and the probe is especially useful. This is especially useful since selectivity could be preserved, as the Tm is reduced by choosing a(n-x)-mer oligonucleotide instead of an n-mer oligonucleotide.

Therefore, a further subject of the invention is a method for the determination of the presence, absence or amount of a nucleic acid in a sample comprising the steps:
providing primers, a first primer being essentially complementary to a first binding sequence of said nucleic acid, and the second primer being essentially complementary to a binding sequence of a complement of this nucleic acid, and a probe being complementary to the nucleic acid or the complement thereof between the binding sequences of said primers, said probe being labelled at different subunits by at least two different reporter groups,
subjecting the sample with said primers and said probe under conditions favouring extention of said primers and separating said reporter groups from each other by disintegrating the probe, and
determining the extent of disintegration of the probe via at least one of said reporter groups, wherein at least one of said primer or/and probe are a nucleic acid binding compound as defined above. Preferably, the melting point of the primers and the probe will be selected such that the $T_m$'s are similar, but that the $T_m$ of the probe is higher than those of the primers.

In another embodiment, the nucleic acid binding compound of the invention can be used as a immobilizable or immobilized probe for binding any nucleic acids to a solid phase. Modes to immobilize the compound are disclosed above. In an assay, it is either possible to immobilize the compound before contacting it with the sample or during contacting the sample with a solid phase, or even after contacting the sample with the solid phase. In each of these cases, the nucleic acid to be determined will be bound to the solid phase and preferably, any substituents of the sample not to be determined may be washed away from the solid phase, while the compounds and the nucleic acid will remain bound. Thereafter, the hybrid bound to the solid phase can be determined by known methods, for example by using detectably labelled probe as outlined above or by direct determination of the hybrid, for example by contacting the hybrid with the intercallating dyes and measuring the change on the solid phase.

In another embodiment, the immobilized probe is used to isolate or purify a nucleic acid.

Another preferred embodiment uses a nucleic acid binding compound which is both bound to a solid phase and labelled by a detectable reporter group. The label in this case preferably is a group the detectable properties of which will change when the nucleic acid to be determined will bind to the probe. Again, those compounds are known in the art.

The man skilled in the art will be in the position to design the sequence of a nucleic acid binding compound when knowing the sequence of the nucleic acid to which the nucleic acid binding compound is intended to be bound. In almost all cases, the nucleic acid will have a sequence containing all four natural nucleic bases. In this case, it is preferable to choose all bases that when bound to the particulars stretch of the nucleic acid are located at positions capable of base pairing to C, A and T of the nucleic acid to be G, T and A respectively. However, these bases can be replaced by equivalent bases base pairing to the mentioned bases in the nucleic acid. The base being at the position capable of base pairing to G in the nucleic acid, will now be replaced one or more time in the nucleic acid binding compound by a group of I. As outlined in this invention, the group of I can also base pair to other moieties, for example to force the orientation of binding from the antiparallel (regular) mode to the parallel (non-natural) orientation.

A further subject of the present invention is the use of 2-azapurine in a nucleic acid binding compound as a substitute for cytosine, especially for the binding of nucleic acids the bases of which are not only consisting of G.

A further subject of the present invention is the use of 2-azapurine in hybridization reactions of probes with the nucleic acid as a base at the position of the probe base pairing at G in the nucleic acid.

Further subject of the present invention is a binding product of at least one nucleic acid binding compound of the invention and a nucleic acid, the nucleic acid binding compound and the nucleic acid being bound to each other by base pairing in parallel or antiparallel orientation. The binding product can contain one molecule of the nucleic acid and one molecule of the nucleic acid binding compound, which form a duplex, or the binding product can contain three strands, thus being a triplex. The triplex can contain either two molecules of the nucleic acid binding compound and one strand of the nucleic acid, or can contain one nucleic acid binding compound and two molecules of the nucleic acid. Which kind of triplex is formed, is dependent upon the concentration and the complementarity of the nucleic acid binding compound and the nucleic acid.

The present invention provides for the possibility to choose similar Tms for a number of probes with different sequence. Thus, a particular subject of the invention are methods, wherein nucleic acids of different sequences are to be isolated or determined simultaneously.

In a first embodiment, this method is a so-called multiplex method for the isolation or determination of nucleic acids. In this embodiment, probes each containing a sequence complementary to a sequence of one of the nucleic acids (for example, nucleic acids from different viruses, like HCV, HIV and HBV) having a $T_m$ adapted according to the invention (one or more probes containing a group of formula I) are contacted with the sample suspected to contain said nucleic acids. Depending upon the formate, the different nucleic acids can be determined via the hybrids formed with the probes either as a sum or independently.

A second embodiment is based on arrays of probes. Especially, a subject of the invention is a method for the determination of the presence or absence of nucleic acids each comprising a particular sequence in a sample comprising the steps contacting said sample with a solid phase having immobilized on its surface nucleic acid binding compounds each containing a sequence complementary to one of said particular sequences of said nucleic acids, determining on said solid phase the formation of hybrids containing a nucleic acid with a particular sequence and the nucleic acid binding compound containing the complementary sequence characterized in that said at least one of said nucleic acid binding compounds is a compound comprising a backbone, said backbone having attached heterocyclic groups capable of base pairing to natural nucleobases at least one of said heterocyclic groups being one of the naturally occurring nucleobases characterized in that at least one other of said heterocyclic groups is a group of the general formula I.

Methods of this type are either useful when simultaneously testing a sample for the presence or absence of nucleic acids, for example a panel of different bacterial species. In this way, it is not only possible to test for one species after each other batchwise, but to receive sequence information on different nucleic acids simultaneously. Those types of methods are generally known in the art. The present invention, however, has found that the nucleic acid binding compounds of the invention are particularly useful in such kind of assays, as the melting temperature can be adjusted to be very similar for nucleic acid binding compounds of difference sequence or/and length. It is evident that in order to achieve similar melting temperatures of each of the nucleic acid binding compounds, not all of these different compounds need to be modified according to the invention, but the man skilled in the art will modify just those compounds which do not behave like the others, for example by having a much higher melting temperature than the melting temperatures of the other compounds on the same solid phase. With each C replaced according to the invention, the $T_m$ may decrease by between 3 and 6° C., preferably by between 4 and 5° C. In this respect, the man skilled in the art will, compared to the chip technology presently known, has much more flexibility to select the particular sequences used for binding the different nucleic acids. For example, the high G-C content of such regions in nucleic acids to be determined up to now prevented these regions from being useful as target regions for such assays based on probes complementary to these regions. According to the present invention, even these regions, which may be highly specific to the nucleic acid to be determined, can now be used in such assays.

Assays using array technology are generally known to a man skilled in the art, for example, from EP-A-0 476 014. Those solid phases are preferably flat carriers. On their surface, separated by pure surface, arrays, each of the arrays having bound a probe of different sequence directed to a specific particular sequence in a nucleic acid. Depending upon the needs of the actual assay, the sequence of the probe will be essentially complementary to one (or more) of the particular sequences contained in said nucleic acid to be determined. During the assay, each nucleic acid will find the probe on the surface to which it can bind. The determination of the formation of hybrids in each array on the solid phase allows the determination of the presence or absence of nucleic acids containing the particular sequence based on the change of a property in this specific array. Preferably, the evaluation of these changes will be made assisted by a computer programme, which knows in which array which particular sequence is present. One chip can contain from 2 to thousands, or even millions of arrays, each having bound a nucleic acid binding compound having a specific sequence which may be unique. However, it is even possible to determine the presence of a group of different nucleic acids, each having a sequence in common, just by using a nucleic acid binding compound being either relatively unspecific and thus binding different sequences, or by selecting the sequence of the nucleic acid binding compounds such that it is directed to a sequence which is present on different nucleic acids.

In a second, slightly different approach, such arrays can be used to determine the sequence of a nucleic acid by following the so-called "sequencing by hybridization" approach. In this mode, the sample preferably will contain mostly nucleic acids of the same sequence. This can be achieved by isolating the sequence from a mixture in which they were contained or by enriching them in-vitro or in-vivo amplification. The sequence of the nucleic acid binding compounds bound to the solid phase will be selected such that they altogether contain a sequence covering the sequence to be determined in the nucleic acid. Within this sequence, the sequences of each nucleic acid binding compound will overlap by one or more bases. In the determination step of this method, it will be detected to which of these partial sequences the nucleic acid will bind, which will only occur (ideally), if a sequence complementary to the partial sequence is contained on a nucleic acid to be determined. Preferably, the evaluation of the result of the assay will be made by a computer. The computer will thus determine from the partial sequences that are apparently contained in the sequence to be determined, in which series they must have been arranged in the whole nucleic acid. Especially in this kind of assays, the present invention is very helpful, as this approach needs a high number of nucleic acid binding compounds to be fixed on the surface, which can not always take into account the problems occuring with high G-C content. In the present invention, it is therefore possible to sequence even nucleic acids having sequences of low and of high G-C content simultaneously.

It is apparent to a man skilled in the art that any compound as disclosed herein can to some extent be present as tautomers and salts. These tautomers and salts, preferably the alkali salts, most preferred the sodium salts, are within the definition of the formulae and subject to the present invention.

The present invention is explained in more detail by the following examples:

EXAMPLES

General

Monomers: Flash chromatography (FC): at 0.5 bar with silica gel 60 (Merck, Darmstadt, Germany). Solvent systems for FC and TLC: $CH_2Cl_2$-MeOH 85:15 (A), EtOAc-MeOH 3:1 (B), $CH_2Cl_2$-MeOH 80:20 (C), $CH_2Cl_2$—Ac-MeOH 17:1:3 (D), $CH_2Cl_2$-MeOH 9:1 (E), $CH_2Cl_2$-acetone 85:15 (F). Samples were collected with an UltroRac II fractions collector (LKB Instruments, Sweden). Melting points: Büchi SMP-20 apparatus (Büchi, Switzerland). UV spectra: U-3200 spectrophotometer (Hitachi, Japan). NMR spectra: AC-250 and AMX-500 spectrometers (Bruker, Germany); δ values are relative to internal $Me_4Si$ or external $H_3PO_4$. Fluorescence spectra were recorded in $H_2O$ on a F-4500 fluorescence spectrophotometer (Hitachi, Japan). Microanalyses were performed by Mikroanalytisches Laboratorium Beller (Göttingen, Germany).

Oligonucleotides: Oligonucleotides were synthesized with a ABI 392 DNA synthesizer (Applied Biosystems, Germany) according to the standard protocol using the "trityl-off" mode, except for the unmodified oligodeoxynucleotides which were synthesized using the "trityl-on" mode. The coupling yields of modified phosphoramidites were generally 95% on average (trityl conductivity monitoring). The detritylated modified oligomers were purified by ion-exchange chromatography on a Dionex Nucleopac PA-100 HPLC column (4×250 mm, P/N 043010, Dionex GmbH, Idstein, Germany) using the following gradient: 5 min 5% 0.01 M NaOH/ 1.5 M aq. LiCl (X) in 0.01 M NaOH (Y); 25 min 5-30% Y in X; 10 min 30-5% Y in X; 5 min 5% Y in X. Ion-exchange HPLC apparatus: L-4250 UV/VIS detector, L-6250 Intelligent pump and D-2500 integrator (Merck-Hitachi, Germany). The tritylated unmodified oligonucleotides were purified by RP-18 HPLC using the following apparatus and procedure: 250×4 mm RP-18 column (Merck, Germany); Merck-Hitachi HPLC apparatus consisting of a 655 A-12 liquid chromatograph with a 655 A variable wavelength UV monitor and a D-2000 Chromato-Integrator (Merck-Hitachi, Darmstadt, Germany); gradients of 0.1 M ($Et_3NH$)OAc (pH 7.0)/MeCN 95:5 (U) and MeCN (V); gradient I: 0-50 min 0-50% V in U, flow rate 1 mL/min; gradient II: 0-20 min 0-20% V in U; 20-40 min 20-40% V in U, flow rate 1 mL/min. Detritylation was performed by treating the purified oligomers with a 2.5% dichloroacetic acid solution in $CH_2C$ $I_2$ (1 mL) for 5 min. After neutralization with $Et_3N$, evaporation to dryness, followed by co-evaporation with MeOH, the oligomers were again purified by RP-18 HPLC using the above-mentioned device. Gradient: 0-30 min 0-20% V in U, 30-35 min 20% V in U, 35-40 min 20-0% V in U, 40-45 min 0% V in U. Subsequent desalting for all oligonucleotides was performed on an RP-19 HPLC column (4×100 mm) using the apparatus as described above. Solvent for adsorption: $H_2O$, solvent for desorption: MeOH-$H_2O$ 3:2. General flow rate: 1 mL/min. MALDI-TOF Mass spectra of the oligonucleotides were measured on a home-built apparatus using UV laser irradiation at 337 nm for 3 nsec.

The enzymatic hydrolysis of the oligomers was performed as described in Helv. Chim. Acta 1998, 81, 1139-1155, but using a flow rate of 0.6 mL/min. Quantification of the constituents was made on the basis of the peak areas, which were divided by the extinction coefficients of the nucleoside ($\epsilon_{260}$ values: dA 15400, dC 7300, dG 11400, dT 8800, $z^2A_d$ 8200). Snake venom phosphodiesterase EC 3.1.15.1, *Crotallus durissus*) and alkaline phosphatase (EC 3.1.3.1, *E. coli*) used for the enzymatic hydrolysis of oligonucleotides were from Roche Diagnostics GmbH.

Determination of melting curves and thermodynamics: Absorbance vs. temperature profiles were measured on Cary 1 or 1E spectrophotometers (Varian, Australia) with a Cary thermoelectrical controller. The $T_m$ values were measured in the reference cell with a Pt-100 resistor, and the thermodynamic data ($\Delta H°$, $\Delta S°$, $\Delta G°_{298}$) were calculated with the program MeltWin 3.0. Circular dichroism (CD) spectra were recorded on a Jasco 600 (Jasco, Japan) spectropolarimeter, a thermostatically controlled bath (Lauda RCS-6) in a 1-cm cuvette.

Example 1

3-(2-Deoxy-β-D-erythro-pentofuranosyl)-3H-imidazo[2, 1-i]purine (1,$N^6$-Etheno-2'-deoxyadenosine, 5). 2'-Deoxyadenosine monohydrate (1) (5.0 g, 20 mmol) was dissolved in 1M aq. sodium acetate buffer (pH 4.5-5.0, 110 mL) by warming to 40-50° C. To the solution chloroacetaldehyde (50% aq. soln, 7.7 mol/L, 25 mL) was added, and the reaction mixture was stirred for 70 h at room temperature. The yellow solution was evaporated to dryness, and the residue was dissolved in MeOH and filtered to remove inorganic salt. After washing with MeOH the combined filtrate and washings were concentrated in vacuo at 40-50° C. The residue was applied to FC (silica gel 60 H, column: 20×6 cm). Elution with $CH_2Cl_2$-MeOH (85:15) gave a main fraction from which upon evaporation of the solvent and subsequent crystallization from MeOH-EtOAc compd. 5 (3.86 g, 70%) was isolated as colorless crystals. M.p. 138-141° C. TLC (silica gel, EtOAc-MeOH, 3:1): $R_f$ 0.4. UV (MeOH): $\lambda_{max}$ 275 (7300), 265 (7600), 258 (6600), 229 nm (35700). $^1$H-NMR ([D$_6$]DMSO) δ 2.39 (m, 1H, H$_\alpha$—C(2')); 2.70 (m, 1H, H$_\beta$—C(2')); 3.57 (m, 1H, H$_a$—C(5')); 3.67 (m, 1H, H$_b$—C(5')); 3.88 (m, 1H, H—C(4')); 4.43 (m, 1H, H—C(3')); 4.99 (t, 1H, $^3$J(H,H)=5.2 Hz, 5'—OH); 5.38 (d, 1H, $^3$J(H,H)=3.8 Hz, 3'—OH); 6.47 (pt, 1H, $^3$J(H,H)=6.2 Hz, H—C(1')); 7.55 (s, 1H, H—C(11)); 8.07 (s, 1H, H—C(10); 8.53 (s, 1H, H—C(2)); 9.29 (s, 1H, H—C(8)).

Example 2

1-(2-Deoxy-β-D-erythro-pentofuranosyl)-5-amino-4-(imidazol-2"-yl)-imidazole (6). Compound 5 (3.85 g, 14 mmol) was treated with 1N aq. NaOH (60 mL) at room temperature overnight. The reaction mixture was adjusted to pH 7 by addition of 2N aq. HCl and concentrated to a syrup. This was dissolved in absolute MeOH, and the precipitated NaCl was filtered of and washed with MeOH. Filtrate and washings were combined and evaporated. The residue was applied to FC (silica gel 60 H, column: 20×6 cm). Elution with CH$_2$Cl$_2$-MeOH (C) afforded a main zone from which compound 6 (2.70 g, 73%) was obtained as a colorless foam which was used for the next reactions without further purification. An analytical sample was crystallized from MeOH-EtOAc to give colorless spherical crystals; m.p. 91-93° C. (decomp.). TLC (silica gel, CH$_2$Cl$_2$—HOAc-MeOH, 17:1:3): $R_f$ 0.22. UV (MeOH): $\lambda_{max}$ 271 nm (12800). $^1$H-NMR ([D$_6$]DMSO) δ 2.21 (m, 1H, H$_\alpha$—C(2')); 2.47 (m, 1H, H$_\beta$—C(2')); 3.57 (m, 2H, H$_2$—C(5')); 3.84 (m, 1H, H—C(4')); 4.36 (m, 1H, H—C(3')); 6.00 (pt, 1H, $^3$J(H,H)=6.5 Hz, H—C(1')); 6.60 (br. s, NH$_2$); 7.13 (s, 2H, H—C(4)+H—C(5)); 7.55 (s, 1H, H—C(2)); 8.16 (s, NH).

Example 3

3-(2-Deoxy-β-D-erythro-pentofuranosyl)-1H-diimidazo[1,2-c:4',5'-e][1,2,3]-triazine (1, N$^6$-etheno-2-aza-2'-deoxyadenosine, 7). A solution of compound 6 (4.50 g, 17 mmol) in 80% aq. HOAc was treated with sodium nitrite (1.17 g, 17 mmol) in an ice-water bath for 1 h. The reaction mixture was evaporated to a syrup. This was dissolved in H$_2$O and evaporated repeatedly to remove HOAc. The residue was applied to FC (silica gel 60H, column, 20×6 cm). Elution with CH$_2$Cl$_2$-MeOH (85:15) afforded compound 7 (2.50 g, 53%) upon evaporation. M.p. 151-152° C. (decomp.). TLC (silica gel, CH$_2$Cl$_2$-MeOH, 4:1): $R_f$ 0.5. UV (MeOH): $\lambda_{max}$ 282 (3100), 268 (3200), 238 nm (37900). $^1$H-NMR ([D$_6$]DMSO) δ 2.54 (m, 1H, H$_\alpha$—C(2')); 2.85 (m, 1H, H$_\beta$—C(2')); 3.97 (m, 2H, H$_2$—C(5')); 4.00 (m, 1H, H—C(4')); 4.50 (m, 1H, H—C(3')); 4.96 (t, 1H, $^3$J(H,H)=5.4 Hz, 5'—OH); 5.41 (d, 1H, $^3$J(H,H)=4.3 Hz, 3'—OH); 6.69 (pt, 1H, $^3$J(H,H)=6.3 Hz, H—C(1')); 7.85 (d, 1H, $^3$J(H,H)=1.1 Hz, H—C(11)); 8.75 (d, 1H, $^3$J(H,H)=1.1 Hz, H—C(10)); 8.95 (s, 1H, H—C(8)). Anal. calcd. for C$_{11}$H$_{12}$N$_6$O$_3$ (276.25): C, 47.83; H, 4.38; N, 30.42; found: C, 47.71; H, 4.32; N, 30.32.

Example 4

4-Amino-7-(2-deoxy-β-D-erythro-pentofuranosyl)-7H-imidazo[4,5-d][1,2,3]-triazine (2-aza-2'-deoxyadenosine, 2). Compound 7 (0.56 g, 2 mmol) was dissolved in 1M aq. sodium acetate buffer (pH 4.0-4.5, 120 mL) by warming to 40-50° C. To this solution N-bromosuccinimide (2.8 g, 16 mmol) was added, and the reaction mixture was stirred at room temperature overnight. The reaction mixture was evaporated and applied to a Dowex 1×8 ion exchange column (3×12 cm, OH$^-$ form). Elution with H$_2$O (250 mL) gave compound 2 (0.19 g, 38%) as colorless needles which decompose above 185° C. The reaction product was identical with an authentic sample in all respects [21].

Example 5

7-(2-deoxy-β-D-erythro-pentofuranosyl)-7H-imidazo[4,5-d][1,2,3]-triazin-4-one (2-aza-2'-deoxyinosine, 3). Compound 2 (19 mg, 0.076 mmol) was dissolved in H$_2$O and adenosine deaminase (2 µg, from calf intestine, dissolved in glycerole) was added. The reaction mixture was stirred for 18 h at room temperature until 2 had completely disappeared (UV monitoring) and then evaporated to dryness in a Speed-Vac concentrator. UV (H$_2$O): $\lambda_{max}$ 247 (5500), 290 nm (6200). $^1$H-NMR (D$_2$O): 2.49 (m, 1H, H$_\alpha$—C(2')); 2.75 (m, 1H, H$_\beta$—C(2')); 3.41, 3.50 (2m, 2H, H$_2$—C(5')); 4.03 (m, 1H, H—C(4')); 4.51 (m, 1H, H—C(3')); 6.43 (pt, 1H, $^3$J(H,H)=3.2 Hz, H—C(1')); 8.31 (s, 1H, H—C(8)).

Example 6

4-(Benzoylamino)-7-(2-deoxy-β-D-erythro-pentofuranosyl)-7H-imidazo[4,5-d][1,2,3]-triazine (8). Compound 2 (125 mg, 0.5 mmol) was co-evaporated twice with anhydrous pyridine. The residue was suspended in anhydrous pyridine and treated with trimethylsilyl chloride (0.5 mL, 4 mmol). After few minutes of stirring a clear solution was formed. The reaction mixture was stirred at room temperature for 2 h. Next, benzoyl chloride (0.25 mL, 2 mmol) was added, and stirring was continued for another 2 h. The reaction mixture was cooled in an ice-water bath, and HO (1 mL) was added. After 10 min the reaction mixture was treated with aqueous conc. NH$_3$ (0.8 mL) and left for additional 30 min. The mixture was then evaporated to dryness, treated with H$_2$O, and extracted with EtOAc (3×20 mL). The combined extracts were dried (Na$_2$SO$_4$) and applied onto a silica gel column (3×15 cm). Elution was performed with CH$_2$Cl$_2$ (150 mL), followed by CH$_2$Cl$_2$-MeOH (9:1). The nucleoside-containing fractions were evaporated to dryness, and compound 8 was crystallised from MeOH-H$_2$O to give colorless needles (135 mg, 76%). M.p. 208-210° C. (decomp>170° C.). TLC (silica gel, CH$_2$Cl$_2$-MeOH 9:1): $R_f$ 0.31. UV: (10% MeOH in water): $\lambda_{max}$ 233 (15600), 276 nm (16400). $^1$H-NMR ([D$_6$] DMSO): δ 2.97 (2m, 2H, H$_2$—C(2')); 3.69 (m, 2H, H$_2$—C(5')); 4.00 (m, 1H, H—C(4')); 4.57 (m, 1H, H—C(3')); 5.07 (t, 1H, $^3$J(H,H)=4.8 Hz, 5'—OH); 5.49 (d, 1H, $^3$J(H,H)=4.0 Hz, 3'—OH); 6.72 (t, 1H, $^3$J(H,H)=6.5 Hz, H—C(1')); 7.61-7.78 (m, 4H, aromatic-H), 8.16 (d, 2H, aromatic-H); 9.09 (s, 1H, H—C(8)); 11.84 (s, 1H, N—H). Anal. calcd. for C$_{16}$H$_{16}$N$_6$O$_4$ (356.3): C, 52.93; H, 4.41; N, 23.38; found: C, 52.68; H, 4.39; N, 23.07.

Example 7

7-(2-Deoxy-β-D-erythro-pentofuranosyl)-4-{[(dimethylamino)methylidene]-amino}-7H-imidazo[4,5-d][1,2,3]-triazine (9a). To a stirred suspension of compound 2 (63 mg, 0.25 mmol) in MeOH (5 mL) N,N-dimethylformamide dimethylacetal (120 mg, 0.5 mmol) was added. Stirring was continued for 2 h at room temperature. The reaction mixture was evaporated to dryness, and the residue was adsorbed on silica gel. Flash chromatography on a silica gel column (3×10 cm) with CH$_2$Cl$_2$ (100 mL) followed by CH$_2$Cl$_2$-MeOH (9:1) afforded colorless needles (MeOH-H$_2$O, 65 mg, 85%). M.p. 173-175° C. TLC (silica gel, CH$_2$Cl$_2$-MeOH, 9:1): $R_f$ 0.28. UV: (10% MeOH in H$_2$O): $\lambda_{max}$ 234 (13250), 319 nm (29500). $^1$H-NMR ([D$_6$] DMSO): δ 2.84 (2m, 2H, H—C(2')); 3.17, 3.25 (2s, 2H, N—CH$_3$); 3.60 (m, 2H, H$_2$—C(5')); 3.92 (m, 1H, H—C(4')); 4.47 (m, 1H, H—C(3')); 5.05 (t, 1H, $^3$J(H,H)=4.9 Hz, 5'—OH); 5.39 (d, 1H, $^3$J(H,H)=4.0 Hz, 3'—OH); 6.55 (t, 1H, $^3$J(H,H)=6.6 Hz, H—C(1')); 8.79 (s, 1H, N=CH); 9.08 (s, 1H, H—C(8)). Anal. calcd. for $C_{12}H_{17}N_7O_3$ (307.3): C, 46.90; H, 5.58; N, 31.90; found: C, 46.55; H, 5.68; N, 31.66.

Example 8

7-(2-Deoxy-β-D-erythro-pentofuranosyl)-4-{[(di-isobutylamino)methylidene]-amino}-7H-imidazo[4,5-d][1,2,3]-triazine (9b). As described for 9a but using N,N-di-isobutylformamide dimethylacetal. Colorless crystals (72%). M.p. 138-140°C. TLC (silica gel, $CH_2Cl_2$-MeOH, 9:1): $R_f$ 0.40. UV (10% MeOH in water): $\lambda_{max}$ 236 (10100), 325 nm (25850). $^1$H-NMR ([D$_6$]DMSO): δ 0.88, 0.94 (2d, 12 H, $CH_3$); 1.95, 2.20 (2m, 2H, CH); 2.80 (2m, 2H, $H_2$—C(2')); 3.30-3.74 (m, 6H, $H_2$—C(5') and 2 $CH_2$); 4.00 (m, 1H, H—C(4')); 4.45 (m, 1H, H—C(3')); 5.03 (t, 1H, $^3$J(H,H)=4.9 Hz, 5'—OH); 5.37 (d, 1H, $^3$J(H,H)=4.0 Hz, 3'—OH); 6.54 (t, 1H, $^3$J(H,H)=6.4 Hz, H—C(1')); 8.78 (s, 1H, N=CH); 9.10 (s, 1H, H—C(8)). Anal. calcd. for $C_{18}H_{29}N_7O_3$·½$H_2O$ (400.5): C, 53.99; H 7.55; N 24.48; found: C 53.65; H 7.62; N 24.11.

Example 9

7-(2-Deoxy-β-D-erythro-pentofuranosyl)-4-{[(di-n-butylamino)methylidene]-amino}-7H-imidazo[4,5-d][1,2,3]-triazine (9c). As described for 9a but using N,N-di-n-butylformamide dimethylacetal. Colorless needles (75%). M.p. 107-109° C. TLC (silica gel, $CH_2Cl_2$-MeOH, 9:1): $R_f$ 0.42. UV: (10% MeOH in water): $\lambda_{max}$ 235 (10200), 325 nm (25700). $^1$H NMR ([D$_6$]DMSO): δ 0.93 (t, 6H, $CH_3$), 1.33, 1.64, 3.70 (3 m, 12H, —$CH_2$—); 2.45, 2.80 (2m, 2H, $H_2$—C(2')); 3.60 (m, 2H, $H_2$—C(5')); 3.92 (m, 1H, H—C(4')); 4.48 (m, 1H, H C(3')); 5.04 (t, 1H, $^3$J(H,H)=5.8 Hz, 5'—OH); 5.39 (d, 1H, $^3$J(H,H)=4.0 Hz, 3'-OH); 6.55 (pt, 1H, $^3$J(H,H)=6.3 Hz, H—C(1')); 8.78 (s, 1H, N=CH); 9.08 (s, 1H, H—C(8)). Anal. calcd. for $C_{18}H_{29}N_7O_3$ (391.5): C 55.23; H 7.47; N 25.05; found: C 55.36; H 7.66; N 24.97.

Example 10

7-[2-Deoxy-5-O-(4,4'-dimethoxytriphenylmethyl)-β-D-erythro-pentofuranosyl]-4-{[(di-n-butylamino)methylidene] amino}-7H-imidazo[4,5-d][1,2,3]-triazine (10a). Compound 9c (390 mg, 1 mmol) was co-evaporated twice with pyridine, and the oily residue was dissolved in anhydrous pyridine (6 mL). Next, 4,4'-dimethoxytriphenyl-methyl chloride (450 mg, 1.3 mmol) was added, and the reaction mixture was stirred at room temperature for 2 h. Thereupon, MeOH (0.2 mL) was added, and stirring was continued for 15 min. The reaction mixture was poured into 15 mL of an aq. 5% $NaHCO_3$ solution, and this was extracted twice with $CH_2Cl_2$ (30 mL, each). The combined extracts were dried over $Na_2SO_4$, evaporated, and the residue was adsorbed on silica gel. This was applied onto a silica gel 60H— column (4×14 cm) and chromatographed with a $CH_2Cl_2$-acetone gradient (0→25% of acetone, total volume, 600 mL). The nucleoside-containing fractions were pooled and evaporated to obtained compound 10a as solid foam (560 mg, 81%). TLC: (silica gel, $CH_2Cl_2$-acetone, 85:15): $R_f$ 0.15. $^1$H-NMR ([D$_6$] DMSO): 0.93 (t, 6H, $CH_3$); 1.34, 1.63, 3.75 (3m, 12H, —$CH_2$—); 2.95 (2m, 2H, $H_2$—C(2')); 3.51 (m, 2H, $H_2$—C(5')); 3.63, 3.69 (2s, 6H, $OCH_3$); 4.01 (m, 1H, H—C(4')); 4.59 (m, 1H, H—C(3')); 5.45 (d, 1H, $^3$J(H,H)=4.1 Hz, 3'—OH); 6.57 (pt, 1H, $^3$J(H,H)=6.2 Hz, H—C(1')); 6.60-7.30 (m, 13H, phenyl-H); 8.71 (s, 1H, N=CH), 9.07. (s, 1H, H—C(8)). Anal. calcd. for $C_{39}H_{47}N_7O_5$ (693.8): C 67.51; H 6.83; N 14.13; found: C 67.15; H 6.82; N 14.13.

Example 11

7-[2-Deoxy-5-O-(4,4'-dimethoxytriphenylmethyl)-β-D-erythro-pentofuranosyl]-4-{[(di-n-butylamino)methylidene] amino}-7H-imidazo[4,5-d][1,2,3]-triazine-3'-[(2-cyanoethyl)-N,N-diisopropyl phosphoramidite] (10b). To a solution of compound 10a (300 mg, 0.43 mmol) in anhydrous $CH_2Cl_2$ (20 mL) N,N-diisopropylethylamine (145 μL, 0.88 mmol) and chloro-(2-cyanoethoxy)-N,N-diisopropylaminophosphine (143 μL, 0.62 mmol) were added under an Ar atmosphere. After stirring for 20 min at room temperature, a 5% aq. $NaHCO_3$ solution (15 mL) was added and the mixture was extracted with $CH_2Cl_2$ (2×30 mL). The organic layer was dried ($Na_2SO_4$), filtered and evaporated. FC (silica gel, column 5×10 cm, $CH_2Cl_2$/acetone, 85:15) gave a mixture of diastereoisomers of the title compound (300 mg, 78%). TLC (silica gel, $CH_2Cl_2$/acetone, 85:15): $R_f$ 0.71, 0.80. $^{31}$P-NMR ($CDCl_3$): 149.962, 150.223.

Example 12

5'-O-(4,4'-dimethoxytrityl)-6-N-((di-n-butylamino)methylene)-2-aza-2'-deoxyadenosine 3'-[(2-Cyanoethyl)-N,N-(diisopropyl)]phosphoramidite (12) To a solution of 5'-O-(4,4'-dimethoxytrityl)-6-N-((di-n-butylamino)methylene)-2-aza-2'-deoxyadenosine (300 mg, 0.43 mmol) in anh. $CH_2Cl_2$ (20 ml) (i-Pr)$_2$EtN (145 μl, 0.88 mmol) and chloro-(2-cyanoethoxy)(diisopropylamino)phosphine (143 μl, 0.62 mmol) were added. After stirring for 20 min at r. t., a 5% aq. $NaHCO_3$ solution (15 ml) was added and the mixture was extracted with $CH_2Cl_2$ (2×30 ml). The organic layer was dried ($Na_2SO_4$), filtered and evaporated. FC (silica gel, column 5×10 cm, $CH_2Cl_2$/acetone, 85:15) gave a mixture of diastereoisomers NR-411 (300 mg, 77%). TLC (silica gel, $CH_2Cl_2$/acetone, 85:15): $R_f$ 0.71, 0.80. $^{31}$P-NMR ($CDCl_3$): 149.962, 150.223.

Example 13

Synthesis of Nucleic Acid Binding Compounds Using the Monomers of Example 12

The synthesis was performed as outlined in the General section.

Example 14

Determination of Nucleic Acids Using Probes According to Example 13

TABLE 1

$T_m$-Values and Thermodynamic Parameters of Duplex Formation of Oligonucleotides Containing 2-Aza-2'-deoxyadenosine.

| Oligonucleotide | SEQ ID NO: | $T_m$ [° C.] | ΔH [kcal/mol] | ΔS [cal/K mol] | ΔG [kcal/mol] |
|---|---|---|---|---|---|
| 5'-d(TAGGTCAATACT) | 1 | | | | |
| 3'-d(ATCCAGTTATGA) | 2 | 46 | −82 | −230 | −10.4 |

TABLE 1-continued $T_m$-Values and Thermodynamic Parameters of Duplex Formation of Oligonucleotides Containing 2-Aza-2'-deoxyadenosine.

| Oligonucleotide | SEQ ID NO: | $T_m$ [° C.] | ΔH [kcal/ mol] | ΔS [cal/ K mol] | ΔG [kcal/ mol] |
|---|---|---|---|---|---|
| 5'-d(TAGGTC6ATACT) | 3 | | | | |
| 3'-d(ATCCAGTTATGA) | 2 | 42 | −85 | −245 | −9.2 |
| 5'-d(TAGGTC6ATACT) | 3 | | | | |
| 3'-d(ATCCAGGTATGA) | 4 | 46 | −83 | −236 | −9.9 |
| 5'-d(TAGGTC66TACT) | 5 | | | | |
| 3'-d(ATCCAGTTATGA) | 2 | 37 | −76 | −219 | −7.7 |
| 5'-d(TAGGTC66TACT) | 5 | | | | |
| 3'-d(ATCCAGAAATGA) | 6 | 25 | −49 | −141 | −5.7 |
| 5'-d(TAGGTC66TACT) | 5 | | | | |
| 3'-d(ATCCAGCCATGA) | 7 | 20 | −41 | −113 | −5.5 |
| 5'-d(TAGGTC66TACT) | 5 | | | | |
| 3'-d(ATCCAGGGATGA) | 8 | 46 | −74 | −206 | −10.1 |
| 5'-d(TAGGTCAATACT) | 1 | | | | |
| 3'-d(ATCCAGGGATGA) | 8 | 36 | −47 | −127 | −7.4 |
| 5'-d(TAGGTCGGTACT) | 9 | | | | |
| 3'-d(ATCCAGCCATGA) | 7 | 54 | | | |

10 mM Na-cacodylate, 100 mM NaCl, 10 mM $MgCl_2$, pH 7; 5 µM single strand concentration; 6: $z^2A_d$.

The two oligonucleotides 5'-d(TAGGTCAATACT) (SEQ ID NO: 1) and 5'-d(AGTATTGACCTA) (SEQ ID NO: 10) were constructed to form a stable hybrid with a $T_m$ value of 47° C. This duplex is used as a standard to study the influence of modified bases on the duplex structure and stability. As can be seen from Table 1, the replacement of one central dA-dT by a $z^2A_d$-dT base pair reduces the $T_m$ of the duplex by 5°; the exchange of two base pairs reveals a decrease of the $T_m$ by 10°. The reduction of duplex stability is obviously independent from the position of base pair replacement: the duplex having two consecutive $z^2A_d$-dT pairs, exhibits the same $T_m$ as the duplex in which the modified base pairs are separated by three regular ones. Duplex stability is linearly decreased further when the number of $z^2A_d$-dT base pairs is increased; the oligonucleotide containing four modified pairs exhibits a $T_m$ of only 28° C. This result is in striking contrast to findings on oligonucleotides in which dA residues are replaced by 8-aza-2'-deoxyadenosine; here, the introduction of even four $z^8A_d$ residues instead of dA does not exert any influence on the duplex stability.

As can be seen from table 1, the TM of an oligonucleotide having at position 7 a G-C base pair (last line in table 1) has a TM of 54° C. Replacement of two C's in these base pairs by 2-azaadenine yields a TM of 46° C. (7 duplex). The same TM is present when these artificial base pairs are replaced by the natural base pair A-T (first duplex). Moreover, the duplex is having mixed 2-azaadenine/G and A-T base pair (third duplex). From table 1 it can be learned that replacement of one G-C base pair by an artificial base pair of the present invention reduces the TM by between 3 and 5° C., preferably 4° C.

The above described results were found for duplexes with antiparallel chain orientation. The same result, however, was also found for oligonucleotide duplexes with a parallel strand polarity. The chain orientation of naturally-occuring DNA is antiparallel (aps). This orientation can be turned to parallel when the duplex contains isoG$_d$-dC and or isoMe$^5$C$_d$-dG base pairs (Helv. Chim. Acta. 1997, 80, 73-85). As the pairing of dA with dT is ambiguous any natural DNA can be hybridized in the parallel mode when the second strand contains the bases isoguanine, isocytosine, adenine and thymine. As an example, one duplex is given in Table 1. When in this duplex two dA-dT base pairs are replaced by $z^2A_d$-dT, a reduction of the $T_m$ value by 10° is determined which is identical with the results for corresponding antiparallel oligonucleotide duplexes.

The $T_m$ data listed in Table 1 display another interesting feature of the base pairing properties of $z^2A_d$ (2). Stimulated by the finding that replacement of a destabilizing central $z^2A_d$-dT base pair by $z^2A_d$-dG enhances the $T_m$ value of the oligomer back to the value of the unmodified duplex ($T_m$ 46° C.), we investigated the duplex stabilities of oligomers containing mismatches.

Figure 6:
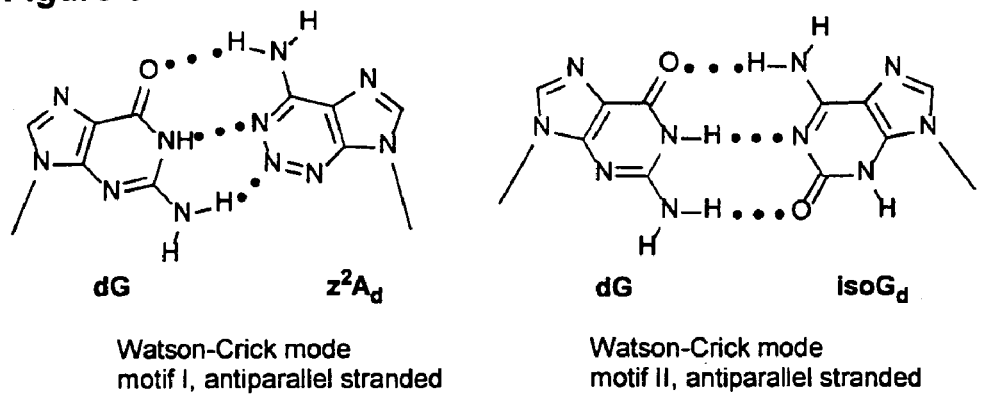
FIG. 6 shows a comparison of the binding of $z^2A_d$ with dG and dG with isoG$_d$ in antiparallel binding.

For this purpose oligodeoxynucleotides were synthesized in which two central $z^2A_d$ residues are placed opposite to either two dT, dA, dC or dG residues. In all cases, except for $z^2A_d$-dG—containing duplexes, the $T_m$ value is significantly decreased—most pronounced for the oligomer with two $z^2A_d$-dC pairs. This oligonucleotide, however, exhibits almost the same value as the unmodified duplex. This prompted us to propose a $z^2A_d$-dG base pair as shown in FIG. 1 and FIG. 6 (motif I). Thus, the present invention can also be used in assays where nucleic acids should be discriminated using mismatches.

The findings on the peculiar base pairing of 2-aza-2'-deoxyadenosine imply that this nucleoside exhibits similar pairing properties as 2'-deoxyisoguanosine (isoG$_d$), the more so as both show a similar hydrogen bonding donor-acceptor pattern when assuming a keto/H—N(3) tautomeric form of 2'-deoxyisoguanosine (FIG. 6, motif II). Indeed, the latter forms a purine-purine base pair with 2'-deoxyguanosine in oligodeoxynucleotides with an antiparallel strand polarity but significantly weaker base pairs with dC and dT, and particularly with dA.

Figure 7:
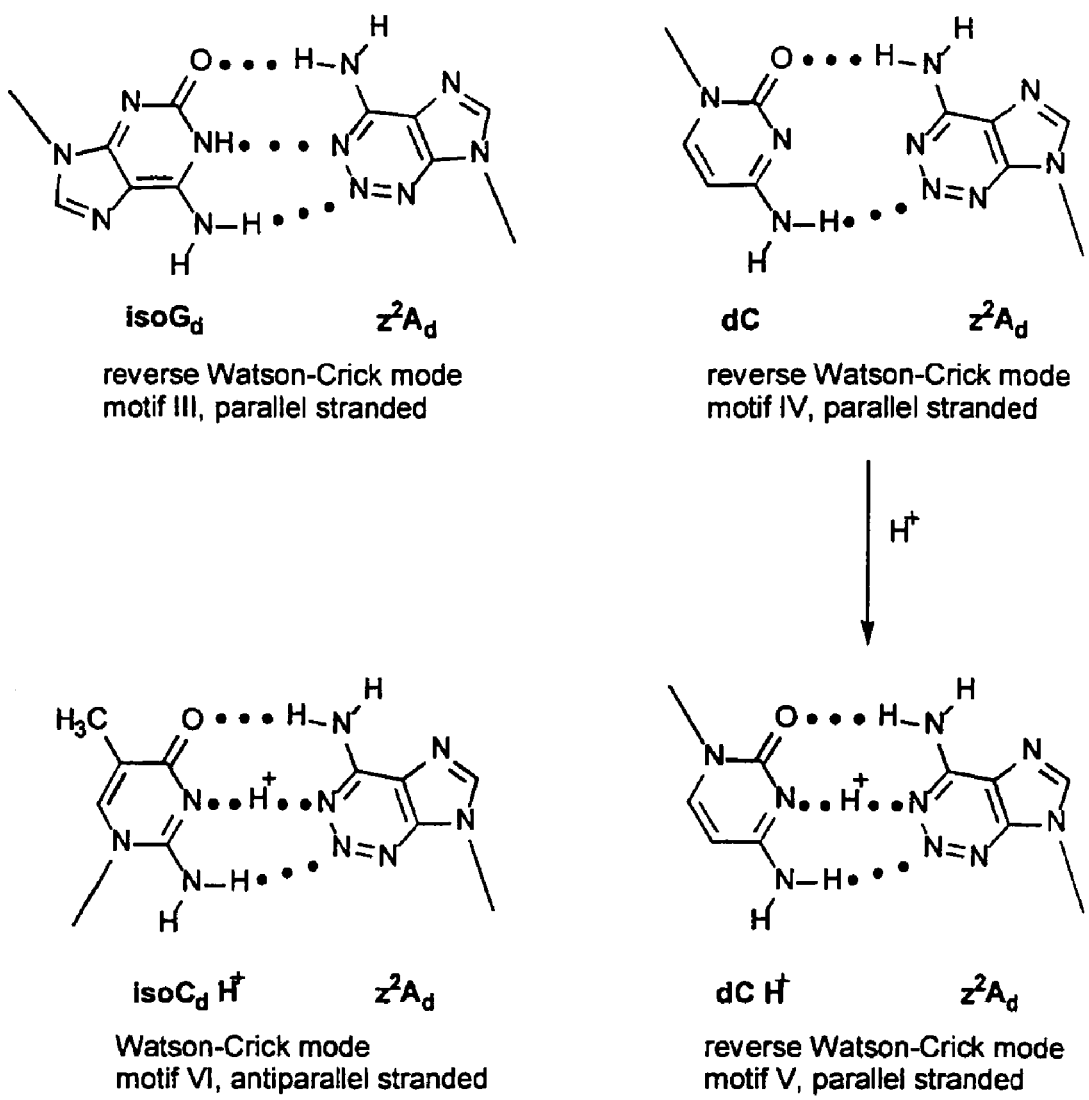
FIG. 7 shows that $z^2A_d$ can also bind in a parallel mode to isoG$_d$, can bind to dC in parallel mode when protonated, and to isoC$_d$ in antiparallel mode if protonated.

With the aid of these results we anticipate that in parallel oriented oligonucleotides 2-aza-2'-deoxyadenosine will form a base pair with isoG$_d$ (FIG. 7, motif III) under neutral conditions as well as with protonated dC (FIG. 7, motif V) in antiparallel arranged duplexes. On the other hand, with protonated 2'-deoxyisocytidine an antiparallel base pair should be formed following the structural motif VI depicted in FIG. 7.

The invention claimed is:

1. A nucleic acid binding compound comprising a backbone, said backbone having attached heterocyclic groups capable of base pairing to natural nucleobases at least one of said heterocyclic groups being one of the naturally occurring nucleobases characterized in that at least one other of said heterocyclic groups is a group of the general formula I

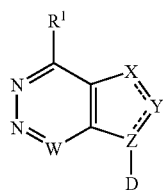

Formula I wherein
W is selected independently from X, Y and Z from the group consisting of N and CR², 
Z is selected from the group consisting of N and C with the proviso that
if Z is N, then
X independently from W and Y is selected from the group consisting of N and CR³, and
Y independently from W and X is selected from the group consisting of N and CR⁴,
and the bond between X and Y is a double bond and the bond between Y and Z is a single bond, and
if Z is C, then
X is NR³³, and
Y is selected from the group consisting of N and CR⁴ and the bond between Z and Y is a double bond and the bond between X and Y is a single bond,
$R^1$, $R^2$, $R^3$ and $R^4$ are independently selected from the group consisting of —H, -halogen, —OR¹³, —SR¹⁹, —(C₁-C₁₀)-alkyl, —(C₂-C₁₀)-alkenyl, —(C₂-C₁₀)-alkynyl, —NO₂, —NR⁵R⁶, -cyano, and —C(=O)R¹¹,
$R^{11}$ is selected from the group consisting of —OH, —(C₁-C₆)-alkoxy, —(C₆-C₂₂)-aryloxy, and NHR¹²,
$R^5$, $R^6$, $R^{12}$, $R^{13}$, $R^{19}$ and $R^{33}$ are selected independently from the group consisting of —H, —(C₁-C₁₀)-alkyl, —(C₂-C₁₀)-alkenyl, —(C₂-C₁₀)-alkinyl, —(C₆-C₂₂)-aryl, a protecting group and a reporter group,
D is the position of attachment of the group to the rest of the nucleic acid binding compound, and
said alkyl, alkenyl and alkynyl being unsubstituted or substituted by one or more moieties selected from the group consisting of -halogen, —SH, —S—(C₁-C₆)-alkyl, —(C₁-C₆)-alkoxy, —OH, —NR⁵R⁶, —COR¹¹, —NH—CONR⁵R⁶, —NH—CSNR⁵R⁶ —[O—(CH₂)ᵣ]ₛ—NR⁵R⁶, and
r and s are independently of each other an integer of 1 to 18.

2. The nucleic acid binding compound of claim 1, wherein the backbone comprises sugar and phosphate moieties.

3. A nucleic acid binding compound of claim 2, wherein the sugar configuration is selected from the group consisting of the α-D-, β-D-, α-L- and β-L-configurations.

4. The nucleic acid binding compound of claim 3, wherein the sugar moiety is a 2'-deoxy-β-D-erythropentofuranosyl moiety.

5. The nucleic acid binding compound of claim 1, wherein $R^1$ is selected from the group consisting of —SH, —(C₁-C₆)-alkoxy, —(C₂-C₆)-alkylmercapto, —NR5R⁶, F and NO₂.

6. The nucleic acid compound of claim 5, wherein $R^1$ is —NR⁵R⁶.

7. The nucleic acid binding compound of claim 1, wherein the backbone comprises one or more moieties of the general formula II

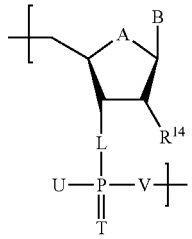

Formula II wherein
A is selected from the group consisting of O, S and N—(C₁-C₁₀)-alkyl,
L is selected from the group consisting of oxy, sulfanediyl and —NR²²—,
T is selected from the group consisting of oxo, thioxo and selenoxo,
U is selected from the group consisting of —OH, —O-reporter group, —SH, —S reporter group —SeH, —(C₁-C₁₀)-alkoxy, (C₁-C₁₀)-alkyl, —(C₆-C₂₂)-aryl, —(C₆-C₁₄)-aryl-(C₁-C₁₀)-alkyl, —NR²³R²⁴, and —O—(C₁-C₁₀)-alkyl-O—(C₁-C₁₀)-alkyl-R²⁵, or wherein —NR²³R²⁴ can together with N be a 5-6-membered heterocyclic ring,
V is selected from the group consisting of oxy, sulfanediyl or —NR²²—,
$R^{14}$ is selected from the group consisting of —H, —OH, —(C₁-C₁₀)-alkoxy, —(C₂-C₁₀)-alkenyloxy, -halogen, -azido, —O-allyl, —O-alkinyl, and —NH₂,
$R^{22}$ is independently selected from the group of —H and —(C₁-C₁₀)-alkyl,
$R^{23}$ and $R^{24}$ are independently selected from the group consisting of —(C₁-C₁₀)-alkyl, —(C₁-C₂₀)-aryl, —(C₆-C₁₄)-aryl-(C₁-C₁₀)-alkyl, —(C₁-C₆)-alkyl-[NH (CH₂)ₑ]ₐ-NR²⁶R²⁷ and a reporter group,
$R^{25}$ is selected from the group consisting of —H, —OH, -halogen, -amino, —(C₁-C₁₈)-alkylamino, —COOH, —CONH₂ and —COO(C₁-C₄)-alkyl and a reporter group,
$R^{26}$ and $R^{27}$ are independently selected from the group consisting from —H, —(C₁-C₆)-alkyl, and —(C₁-C₄)-alkoxy-(C₁-C₆)-alkyl and a reporter group,
c is an integer from 2 to 6,
d is an integer from 0 to 6, and
B is a moiety of formula I,
wherein any alkyl, alkenyl and alkynyl can be substituted or unsubstituted.

8. The nucleic acid binding compound of claim 1, wherein $R^1$ is —NH₂.

9. The nucleic acid compound of claim 1 containing at least one reporter group.

10. The nucleic acid binding compound of claim 1, wherein the backbone comprises a moiety of the general formula III

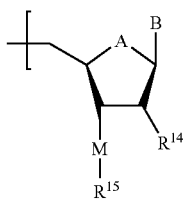

Formula III wherein
- A is selected from the group consisting of O, S and N—$(C_1$-$C_6)$-alkyl,
- M is selected from the group consisting of oxy, sulfanediyl, —$NR^{22}$—, —$(C_1$-$C_{10})$-alkyl-, or —O—$(C_1$-$C_{10})$-alkyl-O—, and —S—$(C_1$-$C_{10})$-alkyl-O— and —$NR^{22}$—$(C_1$-$C_6)$-alkyl-O—,
- $R^{22}$ is selected from the group of —H, —$(C_1$-$C_{10})$-alkyl, a protecting group and a reporter group,
- $R^{14}$ is selected from the group consisting of —H, —OH, —$(C_1$-$C_{10})$-alkoxy, —$(C_2$-$C_{10})$-alkenyloxy, —$(C_2$-$C_{10})$-alkynyloxy, -halogen, -azido, SH, —$(C_1$-$C_{10})$-alkylmercapto and —$NH_2$,
- $R^{15}$ is selected from the group consisting of —H, —$(C_1$-$C_6)$-alkyl, —$(C_2$-$C_{10})$-alkenyl, —$(C_2$-$C_{10})$-alkynyl, —$(C_2$-$C_{10})$-alkyl-carbonyl, —$(C_3$-$C_{19})$-alkenyl-carbonyl, —$(C_3$-$C_{19})$-alkynyl-carbonyl, —$(C_6$-$C_{14})$-aryl-$(C_1$-$C_{10})$-alkyl, a solid phase and a group of formula IV

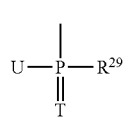

Formula IV wherein
- T is selected from the group consisting of oxo, thioxo and selenoxo, and
- U is selected from the group consisting of —OH, —O-reporter group, —SH, —SeH, —$(C_1$-$C_{10})$-alkoxy, —$(C_1$-$C_{10})$-alkyl, —$(C_6$-$C_{22})$-aryl, —$(C_6$-$C_{14})$-aryl-$(C_1$-$C_{10})$-alkyl, —$NR^{23}R^{24}$, and —O—$(C_1$-$C_{10})$-alkyl-O—$(C_1$-$C_{10})$-alkyl-$R^{25}$, or wherein $NR^{23}R^{24}$ can together with N be a 5-6-membered heterocyclic ring,
- $R^{23}$ and $R^{24}$ are independently selected from the group consisting of —$(C_1$-$C_{10})$-alkyl, —$(C_1$-$C_{20})$-aryl, —$(C_6$-$C_{14})$-aryl-$(C_1$-$C_{10})$-alkyl, —$(C_1$-$C_6)$-alkyl-[NH$(CH_2)_c]_d$—$NR^{26}R^{27}$,
- $R^{25}$ is selected from the group consisting of —H, —OH, -halogen, -amino, —$(C_1$-$C_{18})$-alkylamino, —COOH, —$CONH_2$ and —COO$(C_1$-$C_4)$-alkyl,
- $R^{26}$ and $R^{27}$ are independently selected from the group consisting from —H, —$(C_1$-$C_6)$-alkyl, and —$(C_1$-$C_4)$-alkoxy-$(C_1$-$C_6)$-alkyl
- $R^{29}$ is selected from the group consisting of —$OR^{30}$ and —$SR^{30}$,
- $R^{30}$ is selected from the group consisting of —H, —$(C_1$-$C_{10})$-alkyl, —$(C_2$-$C_{10})$-alkenyl, —$(C_6$-$C_{22})$-aryl, a protecting group, a solid phase and a reporter group
- B is the link to a moiety of formula I,
- wherein any alkyl, alkenyl and alkynyl can be substituted or unsubstituted.

11. The nucleic acid binding compound of claim 1, wherein said backbone comprises a moiety of the formula V wherein

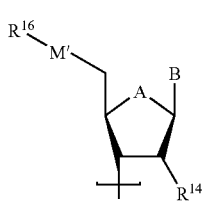

Formula V

- A is selected from the group consisting of O, S and N—$(C_1$-$C_6)$-alkyl,
- M' is selected from the group consisting of oxy, sulfanediyl, —$NR^{22}$—, —$(C_1$-$C_{10})$-alkyl-, or —O—$(C_1$-$C_{10})$-alkyl-O—, and —S—$(C_1$-$C_{10})$-alkyl-O— and —$NR^{22}$—$(C_1$-$C_6)$-alkyl-O—,
- $R^{22}$ is selected from the group of —H, a protecting group, a reporter group and —$(C_1$-$C_{10})$-alkyl,
- $R^{14}$ is selected from the group consisting of —H, —OH, —$(C_1$-$C_{10})$-alkoxy, —$(C_2$-$C_{10})$-alkenyloxy, —$(C_2$-$C_{10})$-alkynyloxy, -halogen, azido, —SH, —S—$(C_1$-$C_6)$-alkylmercapto and $NH_2$,
- $R^{16}$ is selected from the group consisting of —H, —$(C_1$-$C_8)$-alkyl, —$(C_2$-$C_{18})$-alkenyl, —$(C_2$-$C_{18})$-alkynyl, —$(C_2$-$C_{18})$-alkyl-carbonyl, —$(C_3$-$C_{19})$-alkenyl-carbonyl, —$(C_3$-$C_{19})$-alkynyl-arbonyl, —$(C_6$-$C_{14})$-aryl-$(C_1$-$C_8)$-alkyl, a protective group or a compound of formula IV

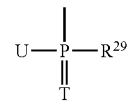

Formula IV wherein
- T is selected from the group consisting of oxo, thioxo and selenoxo,
- U is selected from the group consisting of —OH, —SH, —SeH, —$(C_1$-$C_{10})$-alkoxy, —$(C_1$-$C_{10})$-alkyl, —$(C_6$-$C_{22})$-aryl, —$(C_6$-$C_{14})$-aryl-$(C_1$-$C_{10})$-alkyl, —$NR^{23}R^{24}$, and —O—$(C_1$-$C_{10})$-alkyl-O—$(C_1$-$C_{10})$-alkyl-$R^{25}$, wherein $NR^{23}R^{24}$ can together with N be a 5-6-membered heterocyclic ring,
- $R^{23}$ and $R^{24}$ are independently selected from the group consisting of —$(C_1$-$C_{10})$-alkyl, —$(C_1$-$C_{20})$-aryl, —$(C_6$-$C_{14})$-aryl-$(C_1$-$C_{10})$-alkyl, —$(C_1$-$C_6)$-alkyl-[NH$(CH_2)_c]_d$—$NR^{26}R^{27}$,
- $R^{25}$ is selected from the group consisting of —H, —OH, -halogen, -amino, —$(C_1$-$C_{18})$-alkylamino, —COOH, —$CONH_2$ and —COO$(C_1$-$C_4)$-alkyl,
- $R^{26}$ and $R^{27}$ are independently selected from the group consisting from —H, —$(C_1$-$C_6)$-alkyl, and —$(C_1$-$C_4)$-alkoxy-$(C_1$-$C_6)$-alkyl
- $R^{29}$ is selected from the group consisting of —$OR^{30}$ and —$SR^{30}$,
- $R^{30}$ is selected from the group consisting of —H, —$(C_1$-$C_{10})$-alkyl, —$(C_2$-$C_{10})$-alkenyl, —$(C_6$-$C_{22})$-aryl, a protecting group, a solid phase and a reporter group, and B is the link to a moiety of formula I,
wherein any alkyl, alkenyl and alkynyl can be substituted or unsubstituted.

12. The compound of claim 11, wherein M' is O, $R^{16}$ is H and $R^{14}$ is selected from the group consisting of —H and —OH.

13. The binding product of at least one nucleic acid binding compound of claim 1 and a nucleic acid, the nucleic acid binding compound and the nucleic acid being bound to each other by base pairing in parallel or antiparallel orientation.

* * * * *